(12) United States Patent
Nakamura et al.

(10) Patent No.: US 9,469,623 B2
(45) Date of Patent: Oct. 18, 2016

(54) PREPARATION METHOD FOR OPTICALLY ACTIVE BICYCLIC GAMMA-AMINO ACID COMPOUND

(71) Applicant: DAIICHI SANKYO COMPANY, LIMITED, Tokyo (JP)

(72) Inventors: Yoshitaka Nakamura, Kanagawa (JP); Kazutoshi Ukai, Kanagawa (JP); Takafumi Kitawaki, Kanagawa (JP); Takumi Nakajima, Kanagawa (JP); Yutaka Kitagawa, Kanagawa (JP); Yukito Furuya, Tokyo (JP); Makoto Imai, Kanagawa (JP); Eiji Numagami, Kanagawa (JP); Masakazu Wakayama, Kanagawa (JP); Ayako Saito, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 14/615,972

(22) Filed: Feb. 6, 2015

(65) Prior Publication Data

US 2015/0218123 A1 Aug. 6, 2015

Related U.S. Application Data

(63) Continuation of application No. PCT/JP2014/068101, filed on Jul. 8, 2014.

(30) Foreign Application Priority Data

Jul. 8, 2013 (JP) .................................. 2013-143052

(51) Int. Cl.
*C07C 67/343* (2006.01)
*C07C 211/27* (2006.01)
(Continued)

(52) U.S. Cl.
CPC ............. *C07D 319/06* (2013.01); *C07C 67/00* (2013.01); *C07C 67/343* (2013.01); *C07C 69/608* (2013.01); *C07C 201/12* (2013.01); *C07C 201/16* (2013.01); *C07C 205/50* (2013.01); *C07C 211/27* (2013.01); *C07C 227/04* (2013.01); *C07C 227/42* (2013.01); *C07C 229/32* (2013.01); *C07C 253/00* (2013.01); *C07C 253/10* (2013.01);
(Continued)

(58) Field of Classification Search
CPC . C07D 319/06; C07C 67/343; C07C 69/608; C07C 253/00; C07C 67/00; C07C 227/04; C07C 211/27; C07C 255/47; C07C 205/50; C07C 201/16; C07C 253/30; C07C 227/42; C07C 253/34; C07C 229/32; C07C 201/12; C07C 253/10; C07C 2102/20; C07B 2200/07
See application file for complete search history.

(56) References Cited

U.S. PATENT DOCUMENTS 7,947,738 B2 5/2011 Shimada et al.
8,324,425 B2 12/2012 Kitagawa et al.
(Continued)

FOREIGN PATENT DOCUMENTS

JP 4479974 B2 3/2010
JP 2010-241796 A 10/2010
(Continued)

OTHER PUBLICATIONS

English translation of International Search Report mailed on Aug. 26, 2014, in PCT Application No. PCT/JP2014/068101, 3 pages.

*Primary Examiner* — Samantha Shterengarts
*Assistant Examiner* — Matt Mauro
(74) *Attorney, Agent, or Firm* — Dorsey & Whitney LLP

(57) ABSTRACT

An object of the present invention is to provide an optically active bicyclic γ-amino acid derivative in a high purity. The object can be attained by a mixture of compounds represented by the general formulas (I) and (I'), or a method for producing a compound represented by the general formula (VII) or a salt thereof via the compound (I):

[Formula 1]

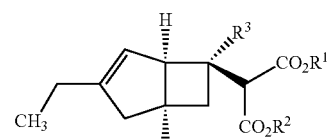

(I)

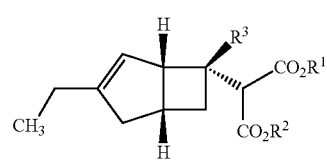

(I')

wherein $R^1$ and $R^2$ each represent a C1-6 alkyl group or the like; and $R^3$ represents a cyano group or the like,

[Formula 2]

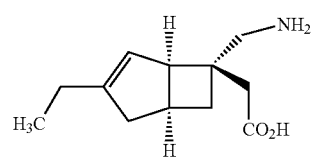

(VII)

16 Claims, No Drawings

(51) Int. Cl.
*C07C 201/16* (2006.01)
*C07C 253/34* (2006.01)
*C07C 253/30* (2006.01)
*C07C 227/42* (2006.01)
*C07C 253/10* (2006.01)
*C07D 319/06* (2006.01)
*C07C 255/47* (2006.01)
*C07C 201/12* (2006.01)
*C07C 205/50* (2006.01)
*C07C 229/32* (2006.01)
*C07C 227/04* (2006.01)
*C07C 67/00* (2006.01)
*C07C 69/608* (2006.01)
*C07C 253/00* (2006.01)

(52) U.S. Cl.
CPC .......... *C07C 253/30* (2013.01); *C07C 253/34* (2013.01); *C07C 255/47* (2013.01); *C07B 2200/07* (2013.01); *C07C 2102/20* (2013.01)

(56) References Cited

U.S. PATENT DOCUMENTS

| | | |
|---|---|---|
| 2003/0078300 A1 | 4/2003 | Blakemore et al. |
| 2003/0220397 A1 | 11/2003 | Bryans et al. |
| 2004/0152779 A1 | 8/2004 | Bryans et al. |
| 2006/0154929 A1 | 7/2006 | Anker et al. |
| 2010/0249229 A1 | 9/2010 | Shimada et al. |
| 2011/0130454 A1 | 6/2011 | Gallop et al. |
| 2012/0071685 A1 | 3/2012 | Kitagawa et al. |
| 2014/0094623 A1 | 4/2014 | Nakamura |
| 2014/0094624 A1 | 4/2014 | Nakamura et al. |
| 2014/0296569 A1 | 10/2014 | Nakamura et al. |
| 2015/0038738 A1 | 2/2015 | Nakamura et al. |

FOREIGN PATENT DOCUMENTS

| | | |
|---|---|---|
| JP | 2013-245215 A | 12/2013 |
| WO | WO 2010/110361 A1 | 9/2010 |
| WO | WO 2013/089188 A1 | 6/2013 |
| WO | WO 2013/154066 A1 | 10/2013 |

PREPARATION METHOD FOR OPTICALLY ACTIVE BICYCLIC GAMMA-AMINO ACID COMPOUND

This application claims the benefit under 35 U.S.C. §111(a) as a continuation application of International Application No. PCT/JP2014/068101, filed Jul. 8, 2014, entitled "Method For Producing Optically Active Bicyclic γ-Amino Acid Derivative," which claims priority to Japanese Patent Application No. 2013-143052, filed Jul. 8, 2013.

TECHNICAL FIELD

The present invention relates to a method for producing an optically active bicyclic compound. According to the present invention, a highly pure bicyclic compound can be efficiently produced.

BACKGROUND ART

Heretofore, $\alpha_2\delta$ ligands have been known as therapeutic drugs for neuropathic pain. Such $\alpha_2\delta$ ligands include, for example, gabapentine and pregabalin. The $\alpha_2\delta$ ligands including these compounds are useful in the treatment of epilepsy and neuropathic pain, etc. (e.g., Patent Literature 1). Other compounds are disclosed in, for example, Patent Literatures 2, 3, and 4.

The present applicant has also previously reported Patent Literatures 5 and 6 which disclose $\alpha_2\delta$ ligands and methods for producing the same.

CITATION LIST

Patent Literature

Patent Literature 1: US 2006/154929
Patent Literature 2: US 2003/220397
Patent Literature 3: US 2004/152779
Patent Literature 4: US 2003/78300
Patent Literature 5: US 2010/249229
Patent Literature 6: US 2012/71685

SUMMARY OF INVENTION

Technical Problem

An object of the present invention is to provide a method for producing an optically active bicyclic compound, particularly, a bicyclic γ-amino acid derivative, or a pharmacologically acceptable salt thereof, or an intermediate for the synthesis of the compound or the salt in a high purity in a stereospecific manner.

Patent Literatures 5 and 6 have reported a method for producing a compound (1-6) as described in Scheme 1.

Scheme 1

[Formula 1]

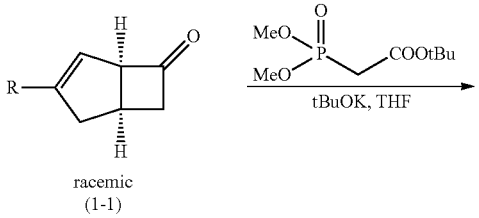

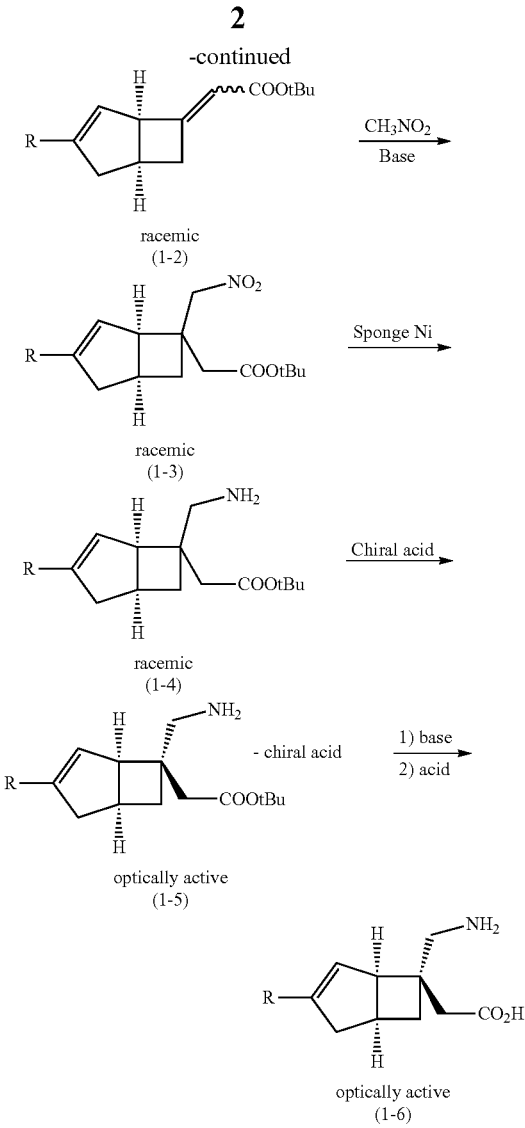

The inventors of the present application have continuously conducted diligent studies to develop efficient methods by focusing on a method for stereocontrolling an asymmetric carbon and a method for producing highly pure compound (1-6) in the method for producing compound (1-6).

The previous production methods are not very good in terms of the stereoselectivity of the quaternary carbon for the production of compound (1-3) from compound (1-2) and cause unfavorable contamination by diastereomers, which, disadvantageously, must be separated in subsequent steps.

In addition, the production of compound (1-6) from compound (1-5) requires heating in the presence of an acid for deprotecting the tert-butyl ester group. In this process, positional isomerization of the double bond proceeds as a secondary reaction. Disadvantageously, the compound (1-6) is thus contaminated by a relatively large amount of the resulting positional isomers. A further challenge to the previous methods is how to obtain highly pure compound (1-6).

Specifically, the problems to be solved by the present invention are how to obtain, with high stereoselectivity, the quaternary carbon that is formed during the conversion of compound (1-2) to compound (1-3), and how to obtain highly pure compound (1-6) by the suppression of related substances as by-products in the production process.

The inventors of the present application have continuously conducted diligent studies to solve these problems and consequently solved the problems, leading to the completion of the present invention.

Solution to Problem

The present invention will be described below.

[1] A mixture of compounds represented by the general formulas (I) and (I'):

[Formula 2]

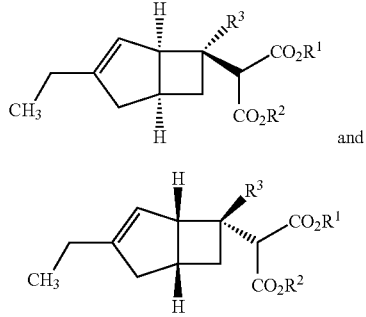

(I)

and (I')

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom), or $R^1$ and $R^2$ are bonded to each other to form an isopropylidene group; and $R^3$ represents a cyano group or a nitromethyl group.

[2] A compound having the configuration of only one of the compounds represented by the general formulas (I) and (I'):

[Formula 3]

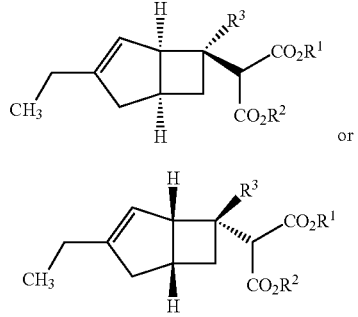

(I)

or (I')

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom), or $R^1$ and $R^2$ are bonded to each other to form an isopropylidene group; and $R^3$ represents a cyano group or a nitromethyl group.

[3] A method for producing a compound represented by the general formula (Ia) (and/or an enantiomer thereof), comprising mixing a compound represented by the general formula (II) (and/or an enantiomer thereof) with an alkali metal salt of hydrogen cyanide in a solvent to produce the compound represented by the general formula (Ia) (and/or an enantiomer thereof):

[Formula 4]

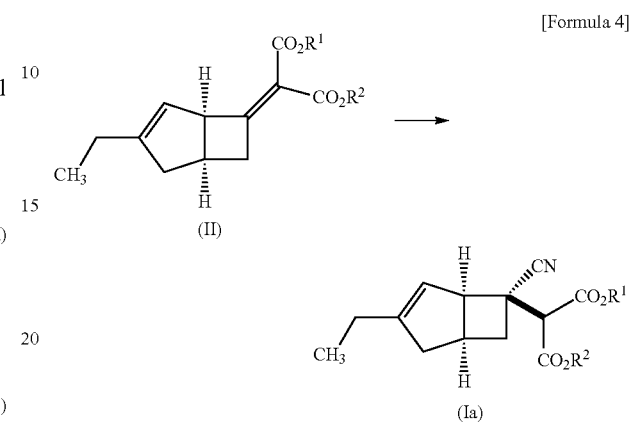

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom), or $R^1$ and $R^2$ are bonded to each other to form an isopropylidene group.

[4] A method for producing a compound represented by the general formula (Ib) (and/or an enantiomer thereof), comprising mixing a compound represented by the general formula (II) (and/or an enantiomer thereof) with nitromethane in the presence of a base in a solvent to produce the compound represented by the general formula (Ib) (and/or an enantiomer thereof):

[Formula 5]

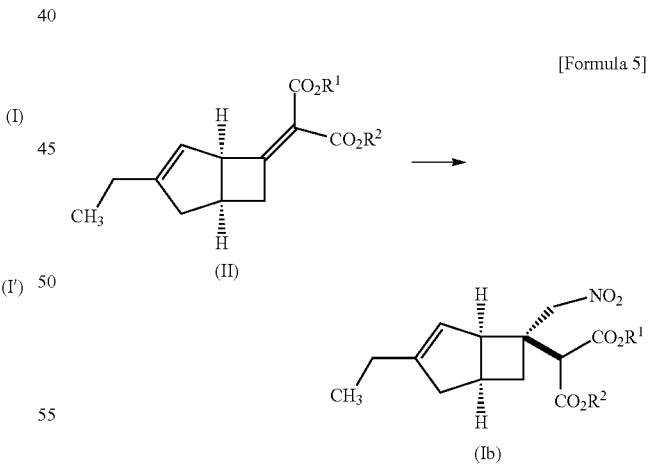

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom), or $R^1$ and $R^2$ are bonded to each other to form an isopropylidene group.

[5] A method for producing a compound represented by the general formula (Ia) or (Ib) (and/or an enantiomer thereof), comprising producing a compound represented by the general formula (II) (and/or an enantiomer thereof) from a compound represented by the general formula (III) (and/or an enantiomer thereof) and a compound represented by the general formula (IV) using a Lewis acid, and then producing the compound represented by the general formula (Ia) or (Ib) (and/or an enantiomer thereof) by a method according to [3] or [4]:

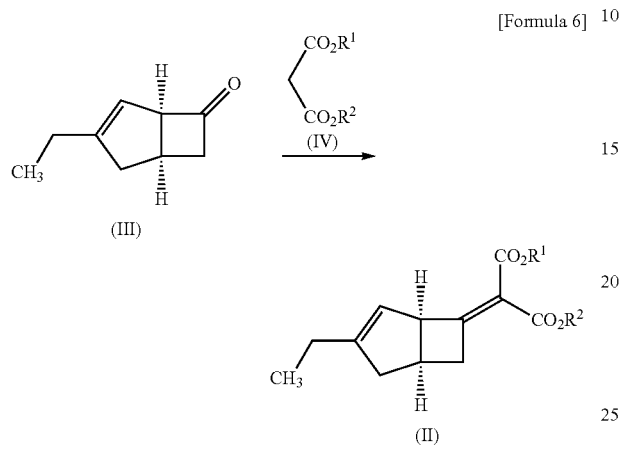

[Formula 6]

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom), or $R^1$ and $R^2$ are bonded to each other to form an isopropylidene group.

[6] A method for producing a compound represented by the general formula (V) (and/or an enantiomer thereof), comprising treating a compound represented by the general formula (I) (and/or an enantiomer thereof) with a base in a solvent:

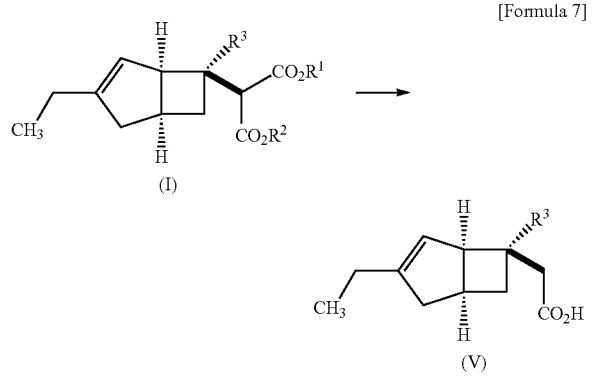

[Formula 7]

wherein $R^1$ and $R^2$ are the same or different and each represent any group selected from a hydrogen atom and a C1-6 alkyl group (preferably, when one of $R^1$ and $R^2$ is any group selected from a C1-6 alkyl group, the other moiety is a hydrogen atom); and $R^3$ represents a cyano group or a nitromethyl group.

[7] A method for separating a compound represented by the general formula (V) and a compound represented by the general formula (V'), comprising allowing a mixture of the compound represented by the general formula (V) and the compound represented by the general formula (V') to form a salt with an optically active organic amine:

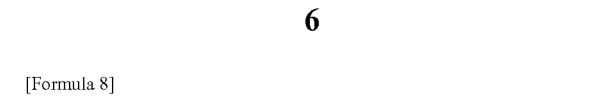

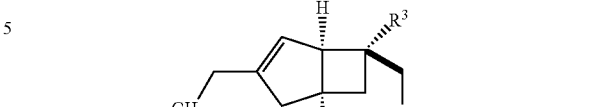

wherein $R^3$ represents a cyano group or a nitromethyl group.

[8] A method for producing a compound represented by the general formula (VI), comprising allowing a compound represented by the general formula (V) to form a salt with an organic amine in the presence of a solvent;

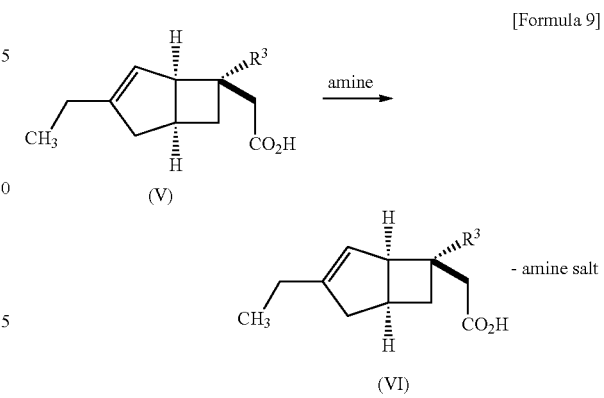

[Formula 9]

wherein $R^3$ represents a cyano group or a nitromethyl group.

[9] The method for producing a compound represented by the general formula (VI) according to [8], wherein $R^3$ is a nitromethyl group, the organic amine used is an optically active organic amine, and a racemic mixture of the compound represented by the general formula (V) is optically resolved.

[10] A method for producing a compound represented by the formula (VII) from a compound represented by the general formula (V) or (VI), comprising (1) reducing the compound represented by the general formula (V) in the presence of a metal catalyst in a solvent under a hydrogen atmosphere, or (2) subjecting a solution of the compound represented by the general formula (V) obtained through the salt dissociation of the compound represented by the general formula (VI) to reduction reaction in the presence of a metal catalyst under a hydrogen atmosphere to produce the compound represented by the formula (VII):

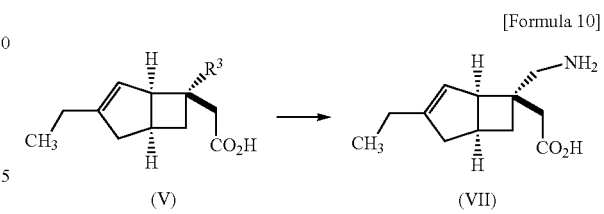

[Formula 10]

-continued

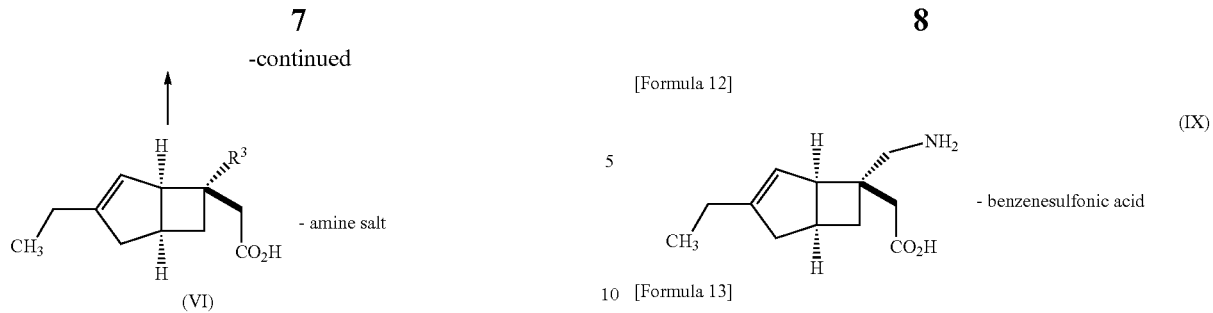

(VI)

wherein R³ represents a cyano group or a nitromethyl group.

[11] The method for producing a compound represented by the formula (VII) according to [10], wherein the metal catalyst is a sponge nickel catalyst or a sponge cobalt catalyst.

[12] The method for producing a compound represented by the formula (VII) according to [11], wherein R³ is a cyano group.

[13] The method for producing a compound represented by the formula (VII) according to [11] or [12], wherein the solvent is water, and the reduction reaction is performed under basic conditions by the addition of a hydroxide of an alkali metal.

[14] A method for producing a compound represented by the general formula (VIII), comprising allowing a compound represented by the formula (VII) produced by a method according to any one of [10] to [13] to form a salt with an organic acid in the presence of a solvent:

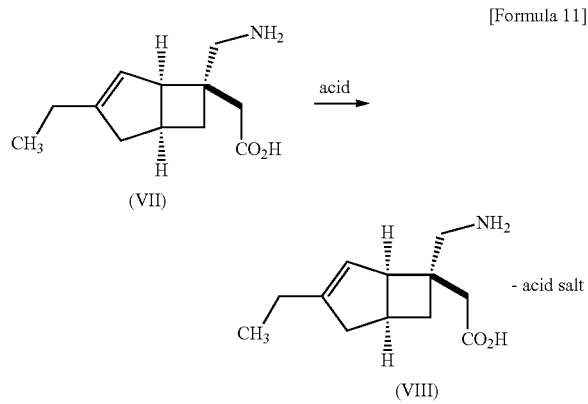

[15] The method for producing a compound represented by the general formula (VIII) according to [14], wherein the organic acid is benzenesulfonic acid.

[16] A compound represented by the formula (IX), wherein the amounts of contaminating impurities are as follows:

content of a diastereomer represented by the formula (X): less than 0.1%, content of an enantiomer represented by the formula (XI): less than 1.0%, and total content of positional isomers of the double bond represented by the formulas (XII) and (XIII): less than 0.5%, wherein each content is calculated from area normalization with respect to the free form (VII) in the formula (IX) in a test by high-performance liquid chromatography:

[Formula 12]

(IX)

- benzenesulfonic acid

[Formula 13]

(X)

(XI)

(XII)

(XIII)

Advantageous Effects of Invention

The present invention is useful because the present invention provides a method for producing an optically active bicyclic compound, particularly, a bicyclic γ-amino acid derivative, or a pharmacologically acceptable salt thereof, or an intermediate for the synthesis of the compound or the salt in a high purity in a stereospecific manner.

DESCRIPTION OF EMBODIMENTS

The C1-C6 alkyl group refers to a linear or branched alkyl group having 1 to 6 carbon atoms. Examples thereof include a methyl group, an ethyl group, a propyl group, an isopropyl group, a butyl group, an isobutyl group, a sec-butyl group, a t-butyl group, a pentyl group, and a hexyl group. The C1-C6 alkyl group is preferably a methyl group, an ethyl group, a propyl group, or a t-butyl group.

Hereinafter, each production step according to the present invention will be described.

Main abbreviations used in the description of the present specification are as listed below.
  CPME: cyclopentyl methyl ether
  THF: tetrahydrofuran
  Me-THF: 2-methyltetrahydrofuran
  DME: 1,2-dimethoxyethane
  DCM: methylene chloride
  AlCl₃: aluminum chloride TiCl₄: titanium tetrachloride
Ti(Oi-Pr)₄: titanium tetraisopropoxide
DMAc: N,N-dimethylacetamide
DMF: N,N-dimethylformamide
CH₃CN: acetonitrile
MeOH: methanol
EtOH: ethanol
DBU: 1,8-diazabicyclo[5.4.0]undec-7-ene
DBN: 1,5-diazabicyclo[4.3.0]non-5-ene
DMSO: dimethyl sulfoxide
MTBE: tert-butyl methyl ether
BsOH: benzenesulfonic acid
EPE: ethyl (diethoxyphosphoryl)acetate
CyNH₂: cyclohexylamine
BnNH₂: benzylamine
t-BuNH₂: t-butylamine
PTLC: preparative thin-layer chromatography

[Step A]

This step involves producing a compound represented by the general formula (II) (and/or an enantiomer thereof) from a compound represented by the general formula (III) (and/or an enantiomer thereof) and a compound represented by the general formula (IV) using a Lewis acid.

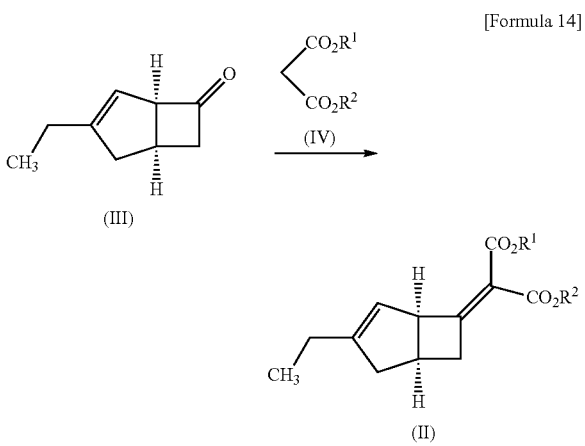

[Formula 14]

wherein $R^1$ and $R^2$ are as defined above.

The solvent used in this step includes: ethers such as CPME, THF, Me-THF, and DME; halogenated hydrocarbons such as DCM; and aromatic hydrocarbons such as toluene. Ether solvents such as CPME, THF, Me-THF, and DME are preferred. CPME or Me-THF is more preferred.

The Lewis acid used in this step is preferably a Lewis acid containing titanium or aluminum as a central metal, more preferably TiCl₄, isopropoxytitanium trichloride, diisopropoxytitanium dichloride, a TiCl₄-2THF complex, a mixture of TiCl₄ and Ti(Oi-Pr)₄ (approximately 3:1), or AlCl₃, or the like, particularly preferably isopropoxytitanium trichloride or a mixture of TiCl₄ and Ti(Oi-Pr)₄ (approximately 3:1).

Although this step does not necessarily require additives other than those described above, an amine compound may be added to the reaction system. The amine compound is preferably pyridine or the like.

This step is carried out at a reaction temperature of usually 50° C. or lower, preferably in the range of 0 to 40° C.

The reaction time of this step is not particularly limited as long as the starting materials are almost completely consumed within the reaction time. The reaction time is usually of the order of 2 hours to 6 hours.

[Step B-1]

This step provides a method for producing a compound represented by the general formula (Ia) (and/or an enantiomer thereof), comprising mixing a compound represented by the general formula (II) (and/or an enantiomer thereof) with an alkali metal salt of hydrogen cyanide in a solvent to produce the compound represented by the general formula (Ia) (and/or an enantiomer thereof).

A feature of this step is that a substantially single diastereomer can be produced by virtue of the addition of a cyano group with very high stereoselectivity.

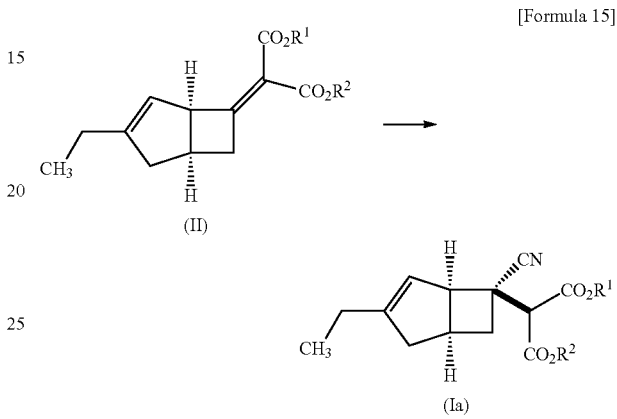

[Formula 15]

wherein $R^1$ and $R^2$ are as defined above.

The alkali metal salt of hydrogen cyanide used in this step is sodium cyanide or potassium cyanide.

The solvent in this step is preferably a C1-C4 alcohol solvent or a nitrogen-containing solvent (e.g., DMAc and CH₃CN), more preferably MeOH or EtOH. Alternatively, such a solvent may be mixed with an ether solvent such as Me-THF or CPME.

The reaction temperature of this step is preferably on the order of 0 to 50° C., more preferably of the order of 20 to 40° C.

The reaction time of this step is not particularly limited as long as the starting materials are almost completely consumed within the reaction time. The reaction time is usually of the order of 2 to 8 hours.

[Step B-2]

This step provides a method for producing a compound represented by the general formula (Ib) (and/or an enantiomer thereof), comprising mixing a compound represented by the general formula (II) (and/or an enantiomer thereof) with nitromethane in the presence of a base in a solvent to produce the compound represented by the general formula (Ib) (and/or an enantiomer thereof).

A feature of this step is that a substantially single diastereomer can be produced by virtue of the addition of a nitromethyl group with very high stereoselectivity.

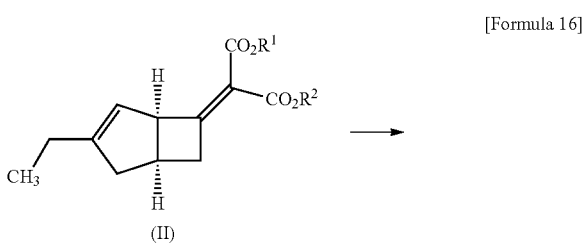

[Formula 16]

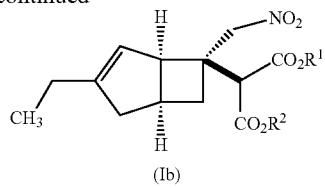

(Ib)

wherein R¹ and R² are as defined above.

The base used in this step can be any of organic and inorganic bases and is preferably DBU, DBN, tetra-n-butylammonium fluoride, or the like, particularly preferably DBU.

The solvent used in this step is preferably an aromatic hydrocarbon solvent (e.g., toluene), a halogenated hydrocarbon solvent (e.g., DCM), a nitrogen-containing solvent (e.g., DMAc and $CH_3CN$), an ester solvent (e.g., ethyl acetate), an ether solvent (e.g., THF), DMSO, or the like, particularly preferably toluene or THF.

The reaction temperature of this step is of the order of 0 to 60° C., more preferably of the order of 20 to 40° C.

The reaction time of this step is not particularly limited as long as the starting materials are almost completely consumed within the reaction time. The reaction time is usually of the order of 2 to 16 hours.

[Step C]

This step provides a method for producing a compound represented by the general formula (V) (and/or an enantiomer thereof), comprising (1) heating a compound represented by the general formula (I) (and/or an enantiomer thereof) in the presence of a base in a solvent to produce a compound represented by the general formula (IV) (and/or an enantiomer thereof) (decarboxylation step), and subsequently (2) hydrolyzing the compound represented by the general formula (IV) (and/or an enantiomer thereof) to produce the compound represented by the general formula (V) (hydrolysis step).

The compound represented by the general formula (IV) (and/or an enantiomer thereof) may be isolated. Typically, the decarboxylation step and the hydrolysis step can be continuously carried out without isolation of the compound represented by the general formula (IV) (and/or an enantiomer thereof) to produce the compound represented by the general formula (V) (and/or an enantiomer thereof).

[Formula 17]

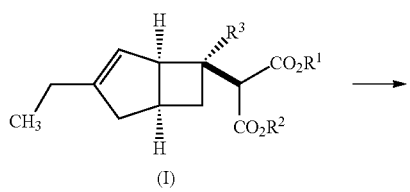

(I)

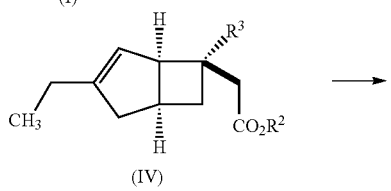

(IV)

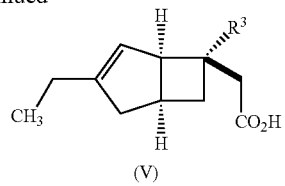

(V)

wherein R¹, R², and R³ are as defined above.

(1) Decarboxylation Step

The reaction in this step is preferably carried out by dissolution of a compound represented by the general formula (I) (and/or an enantiomer thereof) in a solvent and gradual addition of a solution containing a base under heating. The base used in this step is preferably lithium hydroxide, sodium hydroxide, potassium hydroxide, sodium methoxide, sodium ethoxide, sodium tert-butoxide, potassium methoxide, potassium ethoxide, potassium tert-butoxide, or the like, more preferably sodium hydroxide or potassium hydroxide, particularly preferably potassium hydroxide.

The solvent in this step is preferably a C1-C4 alcohol solvent, more preferably MeOH, EtOH, or n-propanol, particularly preferably EtOH. Alternatively, such an alcohol solvent may be supplemented with a small amount of water for the reaction.

The reaction temperature of this step is of the order of 60 to 100° C., preferably of the order of 70 to 80° C.

The reaction time of this step is not particularly limited as long as the starting materials are almost completely consumed within the reaction time. The reaction time is usually of the order of 2 to 20 hours, preferably of the order of 4 to 10 hours.

(2) Hydrolysis Step

This step is carried out by dissolution of the compound represented by the general formula (IV) (and/or an enantiomer thereof) in a solvent and hydrolysis of the ester site in the presence of a base and water. Typically, this step is carried out sequentially from the decarboxylation step using a solution containing the compound represented by the general formula (IV) (and/or an enantiomer thereof) obtained by the decarboxylation step.

The base used in this step is preferably a hydroxide of an alkali metal such as lithium hydroxide, sodium hydroxide, or potassium hydroxide.

Preferred examples of the solvent in this step include: C1-C4 alcohols; ethers such as THF, DME, and 1,4-dioxane; nitrogen-containing solvents such as $CH_3CN$, DMF, and DMAc; and DMSO. The solvent is more preferably MeOH, EtOH, or n-propanol, particularly preferably EtOH.

The reaction temperature of this step is of the order of 0 to 60° C., preferably of the order of 20 to 40° C.

The reaction time of this step is not particularly limited as long as the starting materials are almost completely consumed within the reaction time. The reaction time is usually of the order of 1 to 10 hours, preferably of the order of 1 to 5 hours.

[Step D-1]

This step provides a method for producing a compound represented by the general formula (VI) (and/or an enantiomer thereof), comprising allowing a compound represented by the general formula (V) (and/or an enantiomer thereof) to form a salt with an organic amine in the presence of a solvent. The compound represented by the general formula (VI) (and/or an enantiomer thereof) can be obtained as crystals to thereby efficiently remove by-products into a filtrate and obtain a highly pure product.

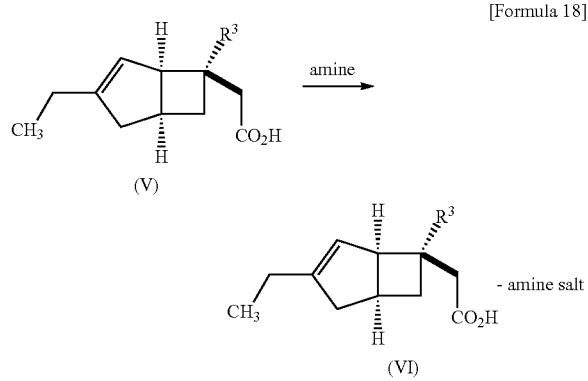

[Formula 18]

wherein R³ is as defined above.

Examples of the solvent used in this step include: ethers such as MTBE, CPME, and THF; aromatic hydrocarbons such as toluene; esters such as ethyl acetate; alcohols such as EtOH and diisopropyl alcohol; nitriles such as $CH_3CN$; ketones such as acetone; and mixed solvents of these solvents with water. The solvent is preferably toluene, ethyl acetate, $CH_3CN$, or MTBE, more preferably toluene or MTBE.

When the substituent represented by R³ is a cyano group, the organic amine used in this step is preferably benzylamine, cyclohexylamine, dicyclohexylamine, (R)-1-phenylethylamine, tert-butylamine, or the like, more preferably cyclohexylamine, benzylamine, or tert-butylamine. When the substituent represented by R³ is a nitromethyl group, the organic amine is benzylamine or (R)-1-phenylethylamine.

The organic amine is used at approximately 0.9 to 1.5 equivalents with respect to the compound represented by the general formula (V) (and/or an enantiomer thereof).

The reaction temperature of this step is of the order of, for example, 0 to 50° C., preferably of the order of 0 to 30° C. (more preferably 0 to 5° C.) for aging of the crystals. Then, the compound represented by the general formula (VI) is obtained by filtration.

The time required for the salt formation in this step is not particularly limited and is usually of the order of 2 to 24 hours.

[Step D-2]

This step provides a method for producing a compound represented by the general formula (VIa), comprising allowing a compound represented by the formula (Va) (and/or an enantiomer thereof) to form a salt with an optically active organic amine to thereby carry out optical resolution.

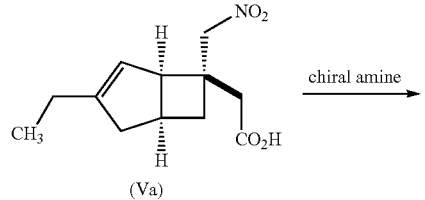

[Formula 19]

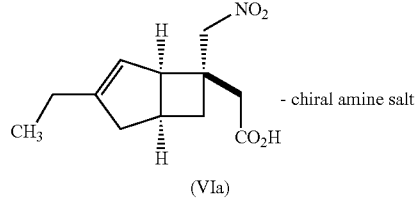

Examples of the solvent used in this step include: ethers such as MTBE, CPME, and THF; aromatic hydrocarbons such as toluene; esters such as ethyl acetate; alcohols such as EtOH and diisopropyl alcohol; nitriles such as $CH_3CN$; ketones such as acetone; and mixed solvents of these solvents with water. The solvent is preferably toluene, ethyl acetate, $CH_3CN$, or MTBE, more preferably toluene or MTBE.

The optically active organic amine used in this step is preferably (1R,2R)-trans-1-amino-2-indanol, (S)-2-phenylglycinol, (R)-1-(p-toluyl)ethylamine, (1R,2S)-2-amino-1,2-diphenylethanol, (S)-1-(2-naphthyl)ethylamine, (R)-1-(4-bromophenyl)ethylamine, (1S,2R)-(+)-1-amino-2-indanol, L-phenylalaninol, or the like, more preferably (1R,2R)-trans-1-amino-2-indanol or (S)-2-phenylglycinol.

The optically active organic amine is used at 0.5 to 1.1 equivalents with respect to the compound represented by the general formula (Va) (and/or an enantiomer thereof).

The reaction temperature of this step is of the order of, for example, 0 to 50° C., preferably of the order of 10 to 30° C. for aging of the crystals. Then, the compound represented by the formula (VIa) is obtained by filtration.

The time required for the salt formation in this step is not particularly limited and is usually of the order of 4 to 48 hours.

This step employs any of the following methods:

(1) a method of allowing the optically active amine mentioned above to act on the compound represented by the formula (Va) (and/or an enantiomer thereof) to directly obtain a compound represented by the formula (VIa) having the desired configuration; and (2) a method of first allowing an optically active amine such as kinin, (1S,2S)-trans-1-amino-2-indanol, or (R)-2-phenylglycinol to act on the compound represented by the formula (Va) (and/or an enantiomer thereof) to temporarily deposit enantiomers having an unnecessary configuration, filtering off the deposits, subsequently allowing an optically active amine such as (1R,2R)-trans-1-amino-2-indanol or (S)-2-phenylglycinol to act on a compound obtained from the filtrate to deposit and obtain a salt of a compound represented by the formula (VIa) having the desired configuration.

The compound represented by the general formula (Va) used in step D-1 or step D-2 can be produced according to step A-C or may be produced by other methods known in the art as shown in Patent Literature 5 (scheme given below).

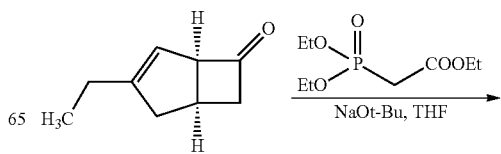

[Formula 20]

-continued

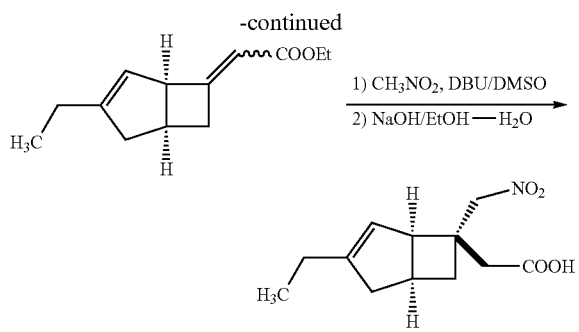

A specific production method based on this method will be described later in the Reference Examples.

[Step E]

This step provides a method for producing a compound represented by the formula (VII) (and/or an enantiomer thereof) from a compound represented by the general formula (V) or (VI) (and/or an enantiomer thereof), comprising reducing the compound represented by the general formula (V) (and/or an enantiomer thereof) in the presence of a metal catalyst in a solvent under a hydrogen atmosphere, or subjecting a solution of the compound represented by the general formula (V) (and/or an enantiomer thereof) obtained through the salt dissociation of the compound represented by the general formula (VI) (and/or an enantiomer thereof) to reduction reaction in the presence of a metal catalyst under a hydrogen atmosphere to produce the compound represented by the formula (VII).

[Formula 21]

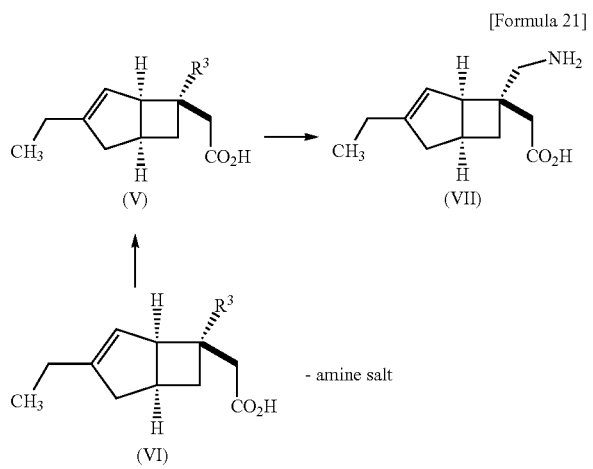

(1) Salt Dissociation Step

The compound represented by the general formula (VI) (and/or an enantiomer thereof) is suspended in an organic solvent. The suspension is washed with an aqueous solution supplemented with an acid. An organic layer can be separated to obtain a solution containing a compound represented by the general formula (V) (and/or an enantiomer thereof).

Examples of the solvent used in this step include: aromatic hydrocarbons such as toluene; ethers such as MTBE; and esters such as ethyl acetate. The solvent is preferably toluene or MTBE.

The acid used in this step is not particularly limited, and hydrochloric acid, sulfuric acid, phosphoric acid, citric acid, malonic acid, or the like can be used.

(2) Reduction Reaction Step

This step involves reducing the compound represented by the general formula (V) (and/or an enantiomer thereof) in the presence of a metal catalyst in a solvent under a hydrogen atmosphere to convert the cyano group (or the nitro group) to an amino group, thereby producing a compound represented by the formula (VII). This reaction is usually carried out under neutral or basic conditions.

The solvent used in this step includes: aromatic hydrocarbons such as toluene; ethers such as MTBE and THF; C1-C4 alcohols; and water. The solvent is preferably toluene, MTBE, or water, particularly preferably water.

The metal catalyst used in this step is sponge nickel, sponge cobalt, or palladium-carbon, preferably sponge nickel (e.g., PL-9T, NDT-65, NDT-90, NDHT-90M, NDHT-M3, etc. manufactured by Kawaken Fine Chemicals Co., Ltd., or R-100, R-200, R-205, R-211, R-2311, etc. manufactured by Nikko Rica Corp.) or sponge cobalt (e.g., ODHT-60, OFT-55, etc. manufactured by Kawaken Fine Chemicals Co., Ltd., R-400, R-400K, R-401, R-455, etc. manufactured by Nikko Rica Corp., or A-8B46, etc. manufactured by Johnson Matthey).

When this step is carried out with water as a solvent, a base is usually added to the reaction system. The base used is preferably an inorganic base, particularly preferably a hydroxide of an alkali metal such as lithium hydroxide, sodium hydroxide, or potassium hydroxide.

The yield of this step can be improved by the addition of ammonia water, although addition of ammonia water is not necessarily required.

In this step, the addition of dimethylpolysiloxane can prevent the reaction solution from foaming, although addition of dimethylpolysiloxane is not necessarily required.

The reaction temperature of this step is of the order of 20 to 60° C., preferably of the order of 30 to 50° C.

The reaction time of this step is not particularly limited as long as the starting materials are almost completely consumed within the reaction time. The reaction time is usually of the order of 2 to 12 hours.

In this step, the catalyst is filtered off after the completion of the reaction. The compound represented by the formula (VII) is crystallized by the addition of an acid to the filtrate. The deposits can be filtered and washed to obtain a highly pure product.

[Step F]

This step provides a method for producing a compound represented by the formula (VIII) (and/or an enantiomer thereof), comprising allowing a compound represented by the formula (VII) (and/or an enantiomer thereof) to form a salt with an organic acid in the presence of a solvent.

[Formula 22]

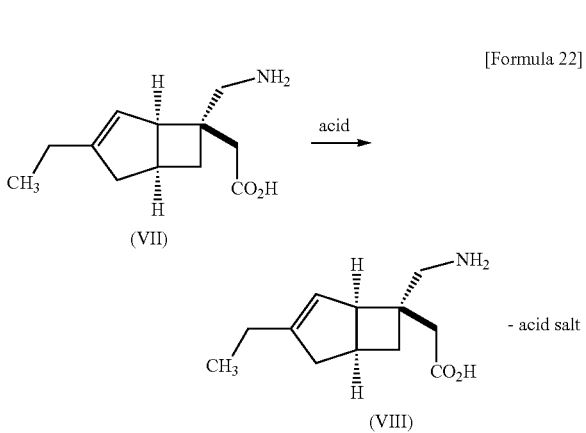

The solvent used in this step is a single or mixed solvent such as water, anisole, aqueous acetone, aqueous CH₃CN, MTBE-water-acetone, anisole-acetic acid, anisole-acetone, anisole-acetic acid-acetone, or acetone-water-CH₃CN, preferably water or anisole.

The organic acid used in this step is a pharmacologically acceptable organic acid, preferably benzenesulfonic acid.

The organic acid is preferably used in this step at approximately 1.00 to 1.10 equivalents with respect to the compound represented by the formula (VII) (and/or an enantiomer thereof).

Typically, this step is carried out in a temperature range of approximately −15 to 50° C. Preferably, the crystals are aged at a temperature of the order of −10 to 30° C., then filtered, and washed to obtain a compound represented by the general formula (VIII) (and/or an enantiomer thereof).

The time required for the salt formation in this step is not particularly limited and is usually of the order of 1 to 24 hours.

In the present invention, the compound represented by the formula (IX) (and/or an enantiomer thereof) produced through steps A to F can be produced as a very highly pure compound. The compound represented by the formula (IX), which can be obtained according to the present invention, usually has the following quality:

content of a diastereomer represented by the formula (X): less than 0.1%, content of an enantiomer represented by the formula (XI): less than 1.0%, and total content of positional isomers of the double bond represented by the formulas (XII) and (XIII): less than 0.5%, wherein each content is calculated from area normalization with respect to the free form (VII) in the formula (IX) in a test by high-performance liquid chromatography.

[Formula 23]

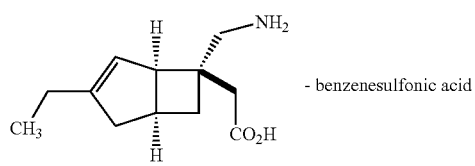
(IX)
- benzenesulfonic acid

[Formula 24]

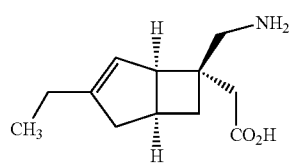
(X)

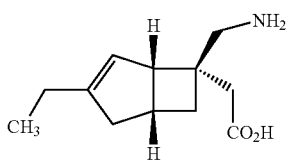
(XI)

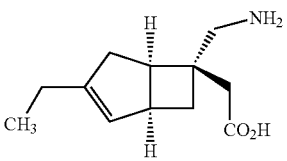
(XII)

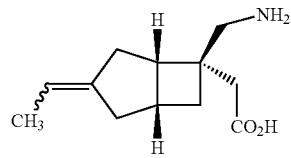
(XIII)

-continued

EXAMPLES

Next, the present invention will be described in detail with reference to the Examples. However, the present invention is not intended to be limited in any way by these Examples.

Tetramethylsilane was used as an internal standard for nuclear magnetic resonance (NMR) spectra. Abbreviations indicating multiplicity are as follows: s=singlet, d=doublet, t=triplet, q=quartet, m=multiplet, and brs=broad singlet.

"R" and "S" in the name of each compound represent the absolute configuration at an asymmetric carbon. Also, "RS" and "SR" represent racemates based on an asymmetric carbon. For example, "(1RS,5SR)-" represents relative configuration at the 1-position and the 5-position indicating only one of the diastereomers and shows that the diastereomer is a racemate.

"E" and "Z" in the name of each compound represent the configurations of positional isomers in the structures of compounds having positional isomerization. Also, "EZ" and "ZE" represent mixtures of positional isomers. The nomenclature follows typical indications in this field.

Abbreviations such as Me, Et, and t-Bu are usually used in this field and represent a methyl group, an ethyl group, and a t-butyl group, respectively.

Example 1

(2EZ)-3-Ethoxy-2-[(1R,5S)-3-ethylbicyclo[3.2.0]hept-3-en-6-ylidene]-3-oxopropanoic acid

[Formula 25]

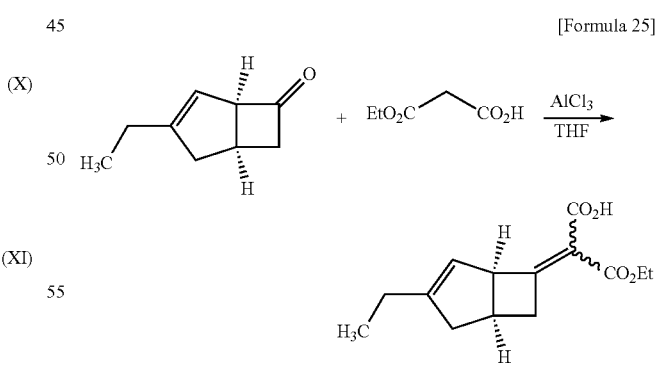

To a solution of malonic acid monoethyl ester (2.9 g, 22.0 mmol) in THF (20 mL), AlCl₃ (3.9 g, 29.4 mmol) was added at −10° C., then (1R,5S)-3-ethylbicyclo[3.2.0]hept-3-en-6-one (2.0 g, 14.7 mmol) was added, and the mixture was stirred at −10° C. for 25 hours. Under ice cooling, water (10 mL) and CPME (10 mL) were added thereto, and the mixture was stirred. Then, an organic layer 1 and an aqueous layer 1 were separated therefrom at 25° C.

Aqueous layer 1 was subjected to extraction with CPME (20 mL) to separate an organic layer 2, which was then combined with organic layer 1 to prepare an organic layer. The combined organic layer was washed with 1 N hydrochloric acid (6 mL) and then concentrated under reduced pressure at an external temperature of 40° C. to obtain the title compound (4.8 g) as a crude product.

$^1$H NMR (CDCl$_3$) (400 MHz): δ=1.07 (3H, t, J=7.6 Hz), 1.35 (1.5H, t, 7.2 Hz), 1.41 (1.5H, t, 7.2 Hz), 2.08-2.16 (2H, m), 2.23-2.31 (1H, m), 2.67-2.75 (1H, m), 2.83-3.05 (2H, m), 3.40-3.48 (0.5H, m), 3.57-3.64 (0.5H, m), 4.27-4.41 (3H, m), 5.29 (0.5H, s), 5.50 (0.5H, s)

Example 2

Dimethyl [(1RS,5SR)-3-ethylbicyclo[3.2.0]hept-3-en-6-ylidene]propanedioate (racemate)

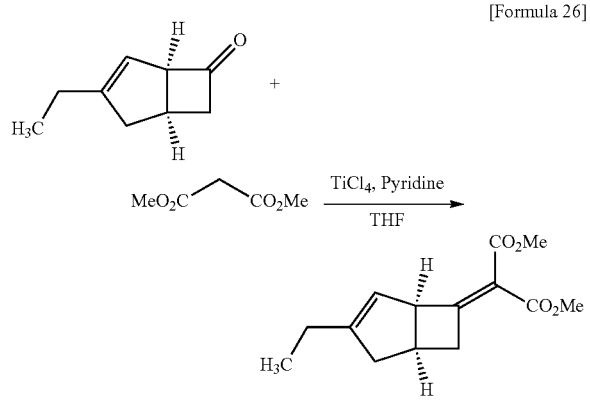

[Formula 26]

To THF (3.2 mL), TiCl$_4$ (0.175 mL, 1.60 mmol) was added at 0° C., and the mixture was stirred for 20 minutes. Subsequently, (1RS,5SR)-3-ethylbicyclo[3.2.0]hept-3-en-6-one (112 mg, 0.819 mmol) and dimethyl malonate (113 μL, 0.989 mmol) were added thereto, and the mixture was stirred for 50 minutes, followed by the addition of pyridine (265 μL, 3.28 mmol). The mixture was stirred at 0° C. for 1 hour, then heated to room temperature, and stirred overnight. The reaction was terminated by the addition of water (6 mL), followed by extraction with toluene (6 mL) three times.

The toluene layer was washed with a saturated aqueous solution of sodium bicarbonate (6 mL) and saturated saline (6 mL). The solvent was distilled off, and the residue was then purified by PTLC (hexane:ethyl acetate=5:1) to obtain the title compound as a colorless oil (135 mg, 65%).

$^1$H NMR (CDCl$_3$) (400 MHz): δ=1.05 (3H, d, J=7.6 Hz), 2.09 (2H, q, J=7.6 Hz), 2.21 (1H, dd, J=16.8, 3.2 Hz), 2.60-2.76 (2H, m), 2.91 (1H, quint, J=7.2 Hz), 3.30 (1H, ddd, J=19.1, 8.4, 3.6 Hz), 3.73 (3H, s), 3.78 (3H, s), 4.29 (1H, m), 5.34 (1H, s).

$^{13}$C NMR (CDCl$_3$) (100 MHz): δ=12.2, 24.2, 32.6, 39.8, 42.7, 51.6, 51.7, 117.5, 120.9, 148.9, 164.6, 164.9, 177.6.

Example 3

Dimethyl [(1R,5S)-3-ethylbicyclo[3.2.0]hept-3-en-6-ylidene]propanedioate

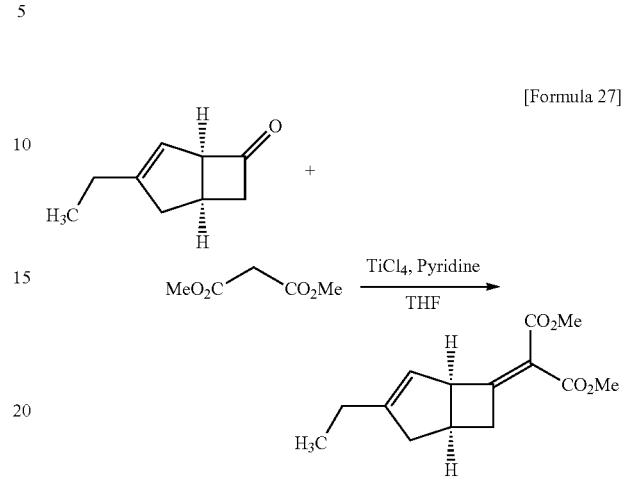

[Formula 27]

To THF (300 mL), TiCl$_4$ (16.0 mL, 146 mmol) was added at 0° C., and the mixture was stirred for 20 minutes. Subsequently, (1R,5S)-3-ethylbicyclo[3.2.0]hept-3-en-6-one (10.04 g, 73.7 mmol) and dimethyl malonate (11.64 g, 88.1 mmol) were added thereto, and the mixture was stirred for 2 hours, followed by the addition of pyridine (23.4 g, 296 mmol). The mixture was stirred at 0° C. for 1.5 hours, then heated to room temperature, and stirred overnight. The reaction was terminated by the addition of water (100 mL), followed by extraction with toluene (100 mL) twice. The toluene layer was washed with saturated saline (100 mL) and concentrated under reduced pressure to obtain a crude product of the title compound as a red-brown oil (22.89 g).

Example 4

Diethyl [(1R,5S)-3-ethylbicyclo[3.2.0]hept-3-en-6-ylidene]propanedioate

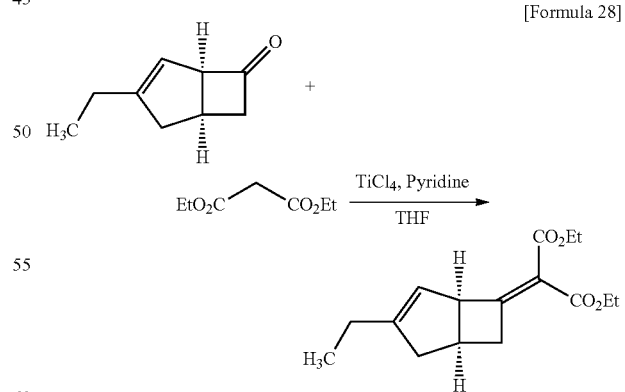

[Formula 28]

To THF (450 mL), TiCl$_4$ (24 mL, 221 mmol) was added at 0° C., and the mixture was stirred for 20 minutes. Subsequently, (1R,5S)-3-ethylbicyclo[3.2.0]hept-3-en-6-one (15.02 g, 110 mmol) and diethyl malonate (19.43 g, 121 mmol) were added thereto, and the mixture was stirred for 2 hours, followed by the addition of pyridine (35.0 g, 442 mmol). The mixture was stirred at 0° C. for 2 hours, then heated to room temperature, and stirred overnight. The reaction was terminated by the addition of water (150 mL), followed by extraction with toluene (150 mL) twice. The toluene layer was washed with saturated saline (90 mL) and concentrated under reduced pressure to obtain a crude product of the title compound as a red-brown oil (43.87 g).

$^1$H NMR (CDCl$_3$) (400 MHz): δ=1.06 (3H, t, J=7.6 Hz), 1.24-1.35 (6H, m), 2.10 (2H, q, J=7.6 Hz), 2.16-2.26 (1H, m), 2.60-2.76 (2H, m), 2.91 (1H, quint, J=7.2 Hz), 3.31 (1H, ddd, J=18.8, 8.4, 3.6 Hz), 4.16-4.30 (1H, m), 5.35 (1H, s).

$^{13}$C NMR (CDCl$_3$) (100 MHz): δ=12.1, 14.18, 14.20, 24.2, 32.7, 39.7, 42.7, 58.3, 60.5, 60.6, 118.2, 121.1, 148.8, 164.2, 164.5, 176.0.

(HPLC Analysis Conditions)

Column: Cadenza CW-C18 (Imtakt, 3 μm, 4.6 mm×150 mm)

Column temperature: 40° C.

Detection wavelength: UV 205 nm

Mobile phase: MeCN:0.1% aqueous AcOH solution=10: 90-80:20 (gradient)

(0-2 min: MeCN 10%, 2-17 min: MeCN 10→80%, 17-25 min: MeCN 80%, 25-30 min: MeCN 80→10%, 40 min: STOP)

Measurement time: 40 min

Flow rate: 1.0 mL/min

Retention time:

(1R,5S)-3-Ethylbicyclo[3.2.0]hept-3-en-6-one: 15.0 min

Diethyl [(1R,5S)-3-ethylbicyclo[3.2.0]hept-3-en-6-ylidene] propanedioate: 19.7 min Example 5

Diethyl [(1RS,5SR)-3-ethylbicyclo[3.2.0]hept-3-en-6-ylidene]propanedioate (racemate)

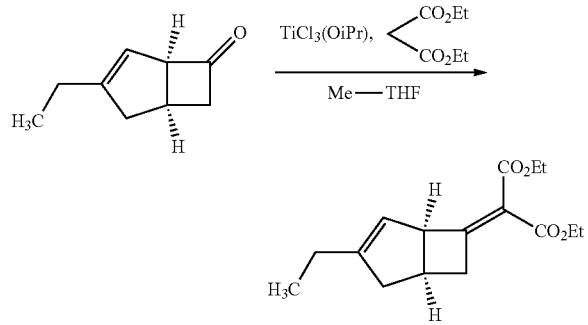

[Formula 29]

To Me-THF (8.1 mL), Ti(Oi-Pr)$_4$ (0.87 mL, 2.97 mmol) was added at 0° C., then TiCl$_4$ (0.98 mL, 8.94 mmol) was added dropwise over 10 minutes, and the mixture was stirred at 0° C. for 1 hour. Subsequently, diethyl malonate (1.00 mL, 6.59 mmol) and (1RS,5SR)-3-ethylbicyclo[3.2.0]hept-3-en-6-one (813 mg, 5.97 mmol) were added thereto, and the mixture was stirred at 20 to 30° C. for 45 hours. The reaction was terminated by the addition of water (10 mL), followed by extraction with toluene (10 mL) twice. After dilution of the organic layer with CH$_3$CN, the title compound was quantified by HPLC (85%).

Example 6

Diethyl [(1RS,5SR)-3-ethylbicyclo[3.2.0]hept-3-en-6-ylidene]propanedioate (racemate)

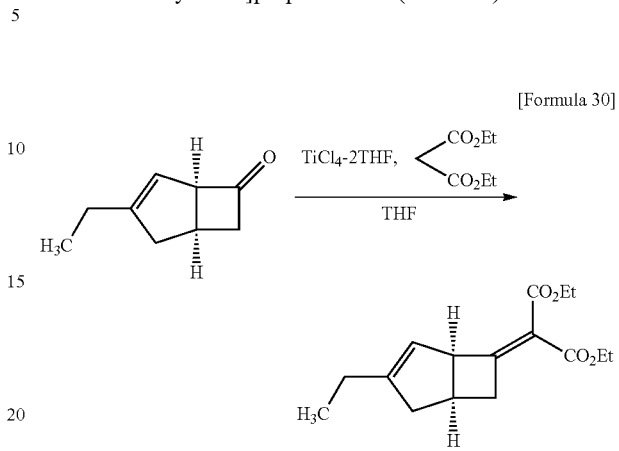

[Formula 30]

To THF (3.1 mL), TiCl$_4$.2THF (509 mg, 1.52 mmol), (1RS,5SR)-3-ethylbicyclo[3.2.0]hept-3-en-6-one (104.2 mg, 0.765 mmol), and diethyl malonate (128 μL, 0.843 mmol) were added at 0° C., and the mixture was stirred for 1.5 hours, followed by the addition of pyridine (248 mL, 3.07 mmol). The mixture was stirred at 0° C. for 1.5 hours, then heated to room temperature, and stirred overnight. The reaction was terminated by the addition of water (6 mL), followed by extraction with toluene (6 mL) three times. The toluene layer was washed with saturated saline (6 mL), and the solvent was distilled off. The title compound in the obtained crude product was quantified by HPLC (230 mg, 86%).

Example 7

Diethyl [(1R,5S)-3-ethylbicyclo[3.2.0]hept-3-en-6-ylidene]propanedioate

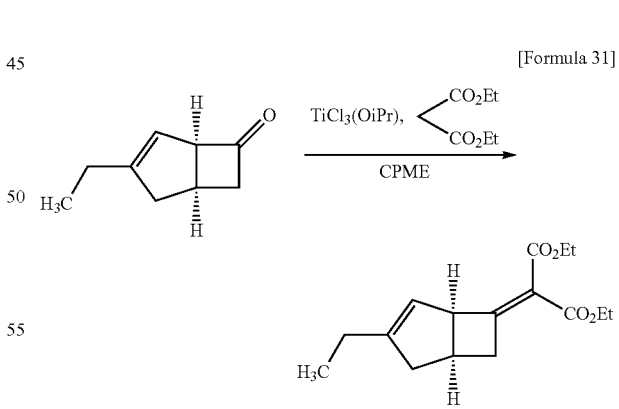

[Formula 31]

To CPME (159 mL), Ti(Oi-Pr)$_4$ (16.0 mL, 54.6 mmol) was added at 0° C., then TiCl$_4$ (18.0 mL, 164 mmol) was added dropwise over 8 minutes, and the mixture was stirred at 0° C. for 1 hour. Subsequently, diethyl malonate (25.72 g, 161 mmol) and (1R,5S)-3-ethylbicyclo[3.2.0]hept-3-en-6-one (19.87 g, 146 mmol) were added thereto, and the mixture was stirred at 30 to 40° C. for 4 hours. The reaction was terminated by the addition of water (100 mL), followed by extraction with toluene (40 mL). The organic layer was concentrated under reduced pressure to obtain a crude product of the title compound as a yellow oil (43.61 g).

Example 8

Di-tert-butyl [(1RS,5SR)-3-ethylbicyclo[3.2.0]hept-3-en-6-ylidene]propanedioate (racemate)

[Formula 32]

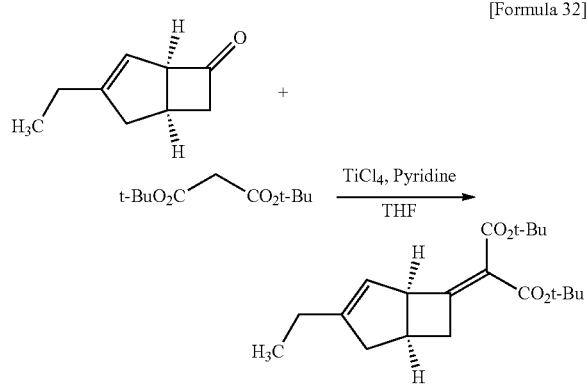

To THF (30 mL), TiCl$_4$ (1.6 mL, 14.7 mmol) was added at 0° C., and the mixture was stirred for 30 minutes. Subsequently, (1RS,5SR)-3-ethylbicyclo[3.2.0]hept-3-en-6-one (1.00 g, 7.34 mmol) and di-tert-butyl malonate (1.91 g, 8.81 mmol) were added thereto, and the mixture was stirred for 1.5 hours, followed by the addition of pyridine (2.2 mL, 29.4 mmol). The mixture was stirred at 0° C. for 3.5 hours, then heated to room temperature, and stirred overnight. The reaction was terminated by the addition of water (10 mL), followed by extraction with toluene (10 mL) twice. The organic layer was washed with saturated saline (10 mL), and the solvent was then distilled off under reduced pressure. The residue was purified by silica gel column chromatography (hexane:ethyl acetate=20:1) to obtain the title compound (2.26 g, 92%).

$^1$H NMR (CDCl$_3$) (500 MHz): δ=1.07 (3H, t, J=7.5 Hz), 1.47 (9H, s), 1.52 (9H, s), 2.06-2.14 (2H, m), 2.16-2.24 (1H, m), 2.60-2.69 (2H, m), 2.90 (1H, quint, J=7.0 Hz), 3.25 (1H, ddd, J=18.6, 8.5, 3.5 Hz), 4.12-4.23 (1H, m), 5.36 (1H, s).

Example 9

5-[(1RS,5SR)-3-Ethylbicyclo[3.2.0]hept-3-en-6-ylidene]-2,2-dimethyl-1,3-dioxane-4-6-dione (racemate)

[Formula 33]

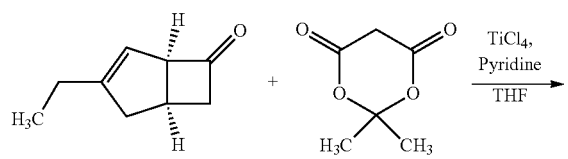

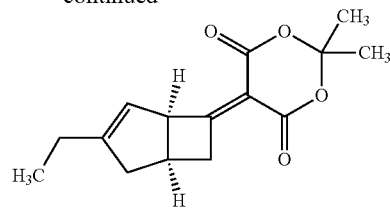

To THF (80 mL), TiCl$_4$ (4.5 mL, 41 mmol) was added at 0° C., and the mixture was stirred for 10 minutes. Subsequently, (1RS,5SR)-3-ethylbicyclo[3.2.0]hept-3-en-6-one (2.81 g, 20.6 mmol) and Meldrum's acid (3.57 g, 24.8 mmol) were added thereto, and the mixture was stirred for 50 minutes, followed by the addition of pyridine (6.53 g, 82.6 mmol). The mixture was stirred at 0° C. for 1.5 hours, then heated to room temperature, and stirred overnight. The reaction was terminated by the addition of water (80 mL), followed by extraction with toluene (50 mL) three times. The organic layer was washed with saturated saline (50 mL) and 1 M hydrochloric acid (10 mL), and the solvent was distilled off. Then, the residue was purified by silica gel column chromatography (hexane:ethyl acetate=9:1-6:1) to obtain the title compound as a white solid (4.51 g, 83.2%).

$^1$H NMR (CDCl$_3$) (400 MHz): δ=1.05 (3H, t, J=7.6 Hz), 1.69 (3H, s), 1.71 (3H, s), 2.11 (2H, q, J=7.6 Hz), 2.20-2.35 (1H, m), 2.65-2.85 (1H, m), 2.92-3.13 (2H, m), 3.47-3.63 (1H, m), 4.45-4.59 (1H, m), 5.43 (1H, s).

$^{13}$C NMR (CDCl$_3$) (100 MHz): δ=12.1, 24.3, 27.59, 27.64, 34.1, 42.3, 42.8, 60.7, 104.4, 108.5, 119.4, 150.3, 160.1, 160.7.

Example 10

Dimethyl [(1R,5S,6R)-6-cyano-3-ethylbicyclo[3.2.0]hept-3-en-6-yl]propanedioate

[Formula 34]

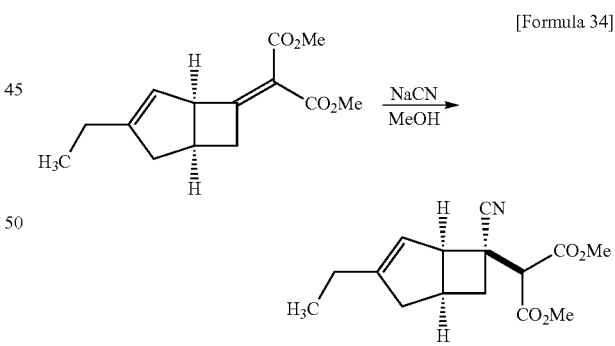

Dimethyl [(1R,5S)-3-ethylbicyclo[3.2.0]hept-3-en-6-ylidene]propanedioate (517 mg, 1.66 mmol) was dissolved in MeOH (5.2 mL). To the solution, sodium cyanide (90 mg, 1.84 mmol) was added at room temperature, and the mixture was stirred at room temperature for 2 hours. The reaction was terminated by the addition of a 10% aqueous acetic acid solution (5 mL), followed by extraction with ethyl acetate (5 mL) three times. The solvent was distilled off under reduced pressure to obtain the title compound as an oil (667 mg).

$^1$H NMR (CDCl$_3$) (400 MHz): δ=1.08 (3H, t, J=7.6 Hz), 1.80 (1H, dd, J=12.4, 8.0 Hz), 2.01-2.22 (3H, m), 2.54 (1H, dd, J=16.8, 7.6 Hz), 2.73 (1H, ddd, J=12.8, 8.8, 2.8 Hz), 3.18 (1H, quint, J=7.6 Hz), 3.67 (1H, s), 3.78 (3H, s), 3.82 (3H, s), 5.16-5.28 (1H, m).
$^{13}$C NMR (CDCl$_3$) (100 MHz): δ=12.2, 24.4, 32.1, 37.5, 39.2, 42.5, 52.9, 53.0, 54.6, 55.0, 118.8, 123.2, 153.9, 166.62, 166.63.

Example 11

Diethyl [(1R,5S,6R)-6-cyano-3-ethylbicyclo[3.2.0]hept-3-en-6-yl]propanedioate

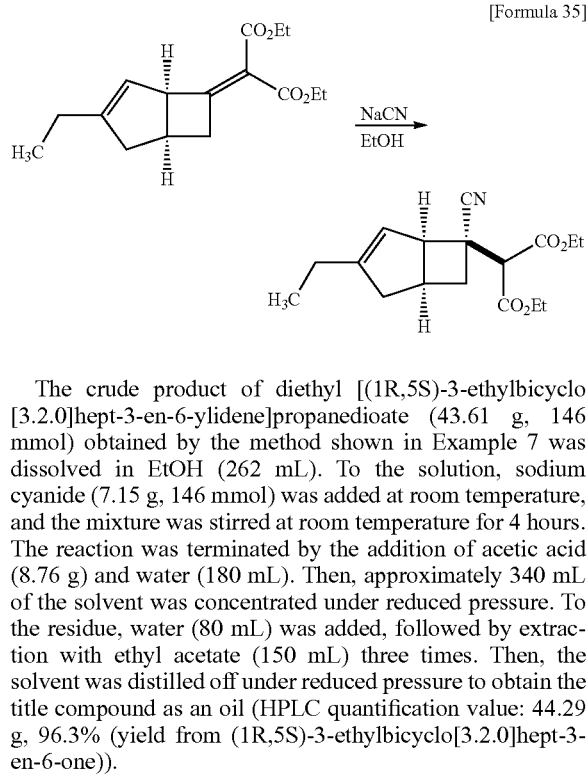

[Formula 35]

The crude product of diethyl [(1R,5S)-3-ethylbicyclo[3.2.0]hept-3-en-6-ylidene]propanedioate (43.61 g, 146 mmol) obtained by the method shown in Example 7 was dissolved in EtOH (262 mL). To the solution, sodium cyanide (7.15 g, 146 mmol) was added at room temperature, and the mixture was stirred at room temperature for 4 hours. The reaction was terminated by the addition of acetic acid (8.76 g) and water (180 mL). Then, approximately 340 mL of the solvent was concentrated under reduced pressure. To the residue, water (80 mL) was added, followed by extraction with ethyl acetate (150 mL) three times. Then, the solvent was distilled off under reduced pressure to obtain the title compound as an oil (HPLC quantification value: 44.29 g, 96.3% (yield from (1R,5S)-3-ethylbicyclo[3.2.0]hept-3-en-6-one)).

$^1$H NMR (CDCl$_3$) (400 MHz): δ=1.07 (3H, t, J=7.6 Hz), 1.28 (3H, t, J=7.2 Hz), 1.31 (3H, t, J=7.2 Hz), 1.80 (1H, dd, J=12.6, 7.6 Hz), 2.01-2.19 (3H, m), 2.53 (1H, dd, J=16.8, 7.6 Hz), 2.72 (1H, ddd, J=12.6, 9.2, 2.8 Hz), 3.16 (1H, quint, J=7.6 Hz), 3.61 (1H, s), 3.67-3.82 (1H, m), 4.15-4.33 (4H, m), 5.21-5.26 (1H, m).
$^{13}$C NMR (CDCl$_3$) (100 MHz): δ=12.2, 14.0, 24.4, 32.2, 37.7, 39.3, 42.5, 55.0, 55.2, 62.00, 62.02, 119.0, 123.3, 153.7, 166.21, 166.23.

(HPLC Analysis Conditions)

Diethyl [(1R,5S,6R)-6-cyano-3-ethylbicyclo[3.2.0]hept-3-en-6-yl]propanedioate quantification method Column: Cadenza CW-C18 (Imtakt, 3 μm, 4.6 mm×150 mm), 40° C.
Detection wavelength: UV 205 nm
Mobile phase: MeCN:0.1% aqueous AcOH solution=10:90-80:20 (gradient)
(0-2 min: MeCN 10%, 2-17 min: MeCN 10→80%, 17-25 min: MeCN 80%, 25-30 min: MeCN 80→10%, 40 min: STOP)
Measurement time: 40 min
Flow rate: 1.0 mL/min Retention time:
Diethyl [(1R,5S,6R)-6-cyano-3-ethylbicyclo[3.2.0]hept-3-en-6-yl]propanedioate: 18.6 min,
Diethyl [(1R,5S)-3-ethylbicyclo[3.2.0]hept-3-en-6-ylidene]propanedioate: 19.7 min Example 12

Diethyl [(1R,5S,6R)-6-cyano-3-ethylbicyclo[3.2.0]hept-3-en-6-yl]propanedioate

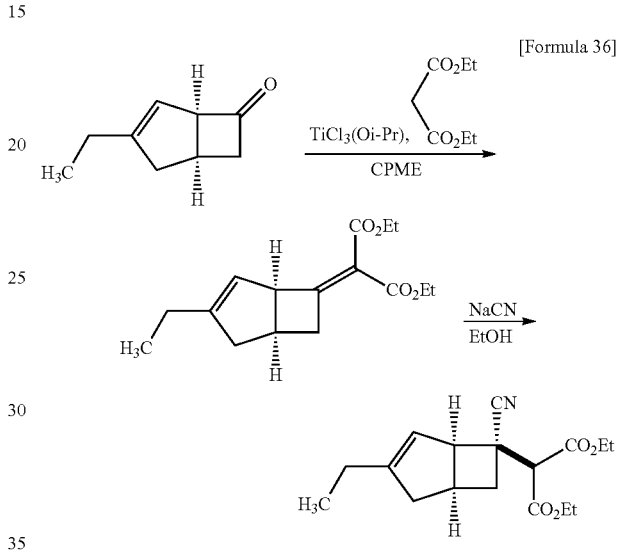

[Formula 36]

Ti(Oi-Pr)$_4$ (25.1 g, 88.11 mmol) was added to CPME (210 mL) under a nitrogen atmosphere, and TiCl$_4$ (29.0 mL, 264 mmol) was added dropwise thereto at 10 to 30° C. over 1 hour. After mixing at 25 to 30° C. for 30 minutes, diethyl malonate (38.8 g, 242 mmol) was added thereto at 3 to 4° C., and the mixture was stirred at 1 to 4° C. for 30 minutes. (1R,5S)-3-Ethylbicyclo-[3.2.0]hept-3-en-6-one (30.0 g, 220 mmol) was added thereto at 1 to 4° C., and the mixture was stirred at 32 to 33° C. for 2.5 hours. Then, cold water (150 mL) was added thereto under ice cooling, and the aqueous layer was removed at room temperature. The organic layer was washed with 1 N hydrochloric acid (60 mL) and then concentrated into 120 mL under reduced pressure at an external temperature of 40 to 45° C. to obtain a CPME solution of diethyl [(1R,5S)-3-ethylbicyclo[3.2.0]hept-3-en-6-ylidene]propanedioate.

To the solution, EtOH (150 mL) was added under a nitrogen atmosphere, then sodium cyanide (10.8 g, 220 mmol) was added, and the mixture was stirred at 27 to 29° C. for 4.5 hours. After cooling to 14° C., a solution containing concentrated sulfuric acid (10.8 g) diluted with water (60 mL) was added to the mixture, and water (150 mL) was further added thereto. The reaction mixture was concentrated into 240 mL under reduced pressure at an external temperature of 35 to 45° C. CPME (60 mL) was added thereto, and the aqueous layer was removed. Then, the organic layer was washed with 20% saline (60 mL) to obtain a CPME solution of the title compound (91.4%, HPLC quantification value).

Example 13

Di-tert-butyl [(1RS,5SR,6RS)-6-cyano-3-ethylbicyclo[3.2.0]hept-3-en-6-yl]propanedioate (racemate)

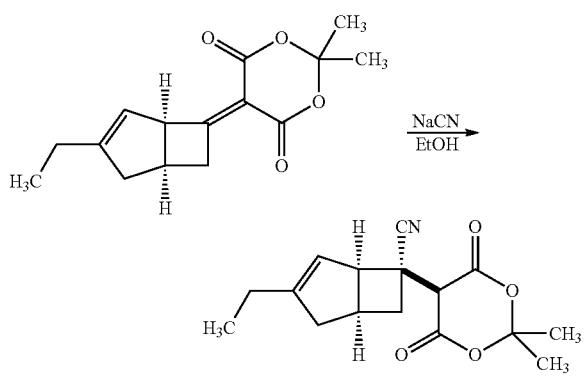

[Formula 37]

Di-tert-butyl [(1RS,5SR)-3-ethylbicyclo[3.2.0]hept-3-en-6-ylidene]propanedioate (5.00 g, 14.9 mmol) was dissolved in DMAc (50 mL). To the solution, sodium cyanide (586 mg, 12.0 mmol) was added at room temperature, and the mixture was stirred at room temperature for 1 hour. The reaction was terminated by the addition of 1 M hydrochloric acid (30 mL), followed by extraction with ethyl acetate (50 mL) three times. The solvent was distilled off under reduced pressure. The residue was purified by silica gel column chromatography (hexane:ethyl acetate=20:1) to obtain the title compound as an oil (5.10 g, 94%).

$^1$H NMR (CDCl$_3$) (400 MHz): δ=1.06 (3H, t, J=7.5 Hz), 1.46 (9H, s), 1.50 (9H, s), 1.78 (1H, dd, J=12.3, 8.0 Hz), 2.00-2.18 (3H, m), 2.51 (1H, dd, J=17.0, 7.5 Hz), 2.68 (1H, ddd, J=12.6, 8.5, 3.0 Hz), 3.13 (1H, quint, J=7.5 Hz), 3.40 (1H, s), 3.65-3.73 (1H, m), 5.24 (1H, s).

Example 14

(1RS,5SR,6RS)-6-(2,2-Dimethyl-4,6-dioxo-1,3-dioxan-5-yl)-3-ethylbicyclo[3.2.0]hept-3-ene-6-carbonitrile (racemate)

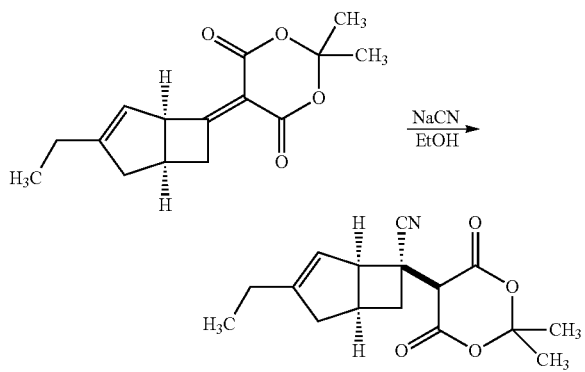

[Formula 38]

5-[(1RS,5SR)-3-Ethylbicyclo[3.2.0]hept-3-en-6-ylidene]-2,2-dimethyl-1,3-dioxane-4,6-dione (100.8 mg, 0.384 mmol) was dissolved in EtOH (1.0 mL). To the solution, sodium cyanide (22.0 mg, 0.449 mmol) was added at room temperature, and the mixture was stirred at room temperature for 3 hours. The reaction was terminated by the addition of a phosphate buffer solution (pH 7) (5 mL), followed by extraction with ethyl acetate (5 mL) three times. The solvent was distilled off under reduced pressure to obtain the title compound as a white solid (23.6 mg, 21.2%).

$^1$H NMR (CD$_3$OD) (400 MHz): δ=1.03 (3H, t, J=7.6 Hz), 1.61 (3H, s), 1.92-2.25 (4H, m), 2.45 (1H, dd, J=16.8, 7.2 Hz), 2.66-2.80 (1H, m), 3.00 (1H, quint, J=7.6 Hz), 3.72-3.87 (1H, m), 4.85 (1H, s), 5.23-5.33 (1H, m).

$^{13}$C NMR (CD$_3$OD) (100 MHz): δ=12.66, 12.69, 25.3, 34.1, 38.8, 39.4, 43.3, 57.0, 75.8, 102.9, 123.67, 123.70, 127.9, 150.5, 167.9.

Example 15

Ethyl [(1RS,5SR,6SR)-3-ethyl-6-(nitromethyl)bicyclo[3.2.0]hept-3-en-6-yl]acetate (racemate)

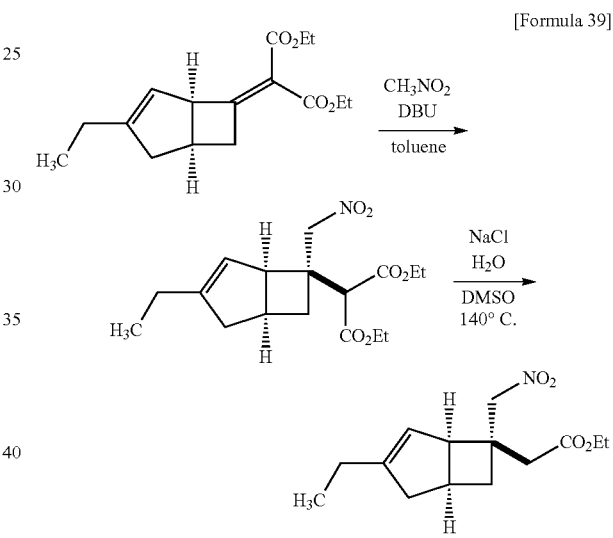

[Formula 39]

Diethyl [(1RS,5SR)-3-ethylbicyclo[3.2.0]hept-3-en-6-ylidene]propanedioate (256.0 mg, 0.920 mmol) was dissolved in toluene (2.5 mL). To the solution, DBU (152 mL) and nitromethane (55 mL) were added, and the mixture was stirred at room temperature for 17 hours. The reaction was terminated by the addition of 1 M hydrochloric acid (5 mL), followed by extraction with ethyl acetate (5 mL) three times. The obtained ethyl acetate solution was washed with saturated saline (5 mL). The solvent was distilled off under reduced pressure to obtain diethyl [(1RS,5SR,6SR)-3-ethyl-6-(nitromethyl)bicyclo-[3.2.0]hept-3-en-6-yl]propanedioate as a pale yellow oil (336.9 mg).

The obtained diethyl [(1RS,5SR,6SR)-3-ethyl-6-(nitromethyl)bicyclo[3.2.0]hept-3-en-6-yl]-propanedioate (336.9 mg) was dissolved in DMSO (3.4 mL). To the solution, water (50 µL, 2.78 mmol) and sodium chloride (64.8 mg, 1.11 mmol) were added, and the mixture was stirred under heating at 140° C. for 10 hours. After cooling to room temperature, the reaction was terminated by the addition of 1 M hydrochloric acid (5 mL), followed by extraction with ethyl acetate (5 mL) three times. Then, the obtained ethyl acetate solution was washed with saturated saline (5 mL).

The solvent was distilled off under reduced pressure to obtain the title compound as a brown oil (261.6 mg, yield through two steps: 72.4%).

Diethyl [(1RS,5SR,6SR)-3-ethyl-6-(nitromethyl)bicyclo[3.2.0]hept-3-en-6-yl]propanedioate $^1$H NMR (CDCl$_3$) (400 MHz): δ=1.08 (3H, t, J=7.6 Hz), 1.17-1.35 (6H, m), 1.73 (1H, dd, J=13.2, 7.6 Hz), 2.05 (1H, d, J=16.4 Hz), 2.05-2.22 (2H, m), 2.42-2.58 (2H, m), 2.75 (1H, quint, J=7.6 Hz), 3.46 (1H, brs), 3.79 (1H, s), 4.09-4.27 (4H, m), 4.96 (2H, s), 5.27 (1H, s).
$^{13}$C NMR (CDCl$_3$) (100 MHz): δ=12.3, 13.97, 14.04, 24.4, 31.6, 36.1, 42.5, 45.6, 53.6, 55.5, 61.49, 61.53, 80.1, 120.7, 152.0, 167.7, 167.8.

Ethyl [(1RS,5SR,6SR)-3-ethyl-6-(nitromethyl)bicyclo[3.2.0]hept-3-en-6-yl]acetate $^1$H NMR (CDCl$_3$) (400 MHz): δ=1.07 (3H, t, J=7.6 Hz), 1.25 (3H, t, J=7.6 Hz), 1.52 (1H, dd, J=12.6, 7.2 Hz), 2.04 (1H, d, J=16.4 Hz), 2.05-2.19 (2H, m), 2.23-2.35 (1H, m), 2.50 (1H, dd, J=15.8, 7.6 Hz), 2.62 (2H, s), 2.86 (1H, quint, J=7.6 Hz), 3.21 (1H, brs), 4.12 (4H, q, J=7.6 Hz), 4.76 (2H, d, J=11.6 Hz), 4.83 (2H, d, J=11.6 Hz), 5.24 (1H, s).

Example 16

Di-tert-butyl [(1RS,5SR,6RS)-3-ethyl-6-(nitromethyl)bicyclo[3.2.0]hept-3-en-6-yl]propanedioate (racemate)

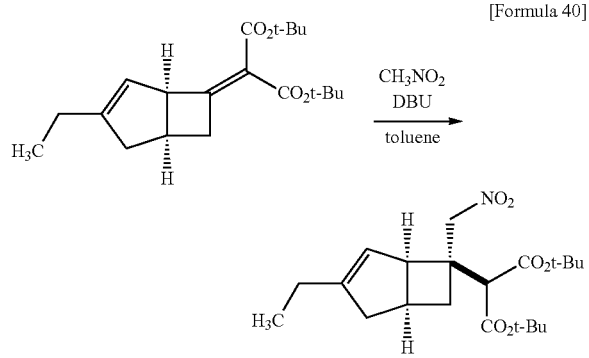

[Formula 40]

Di-tert-butyl [(1RS,5SR)-3-ethylbicyclo[3.2.0]hept-3-en-6-ylidene]propanedioate (2.55 g) was dissolved in toluene (26 mL). To the solution, DBU (1.45 mL) and nitromethane (1.05 mL) were added, and the mixture was stirred at room temperature for 49 hours. The reaction was terminated by the addition of 1 M hydrochloric acid (50 mL), followed by extraction with ethyl acetate (50 mL) three times. The obtained ethyl acetate solution was washed with saturated saline (50 mL). The solvent was distilled off under reduced pressure to obtain the title compound as a pale yellow oil (2.36 g, yield: 78%).

$^1$H NMR (CDCl$_3$) (500 MHz): δ=1.09 (t, 3H, J=7.4 Hz), 1.45 (s, 9H), 1.49 (s, 9H), 1.71 (dd, 1H, J=12.9, 7.4 Hz), 2.03 (d, 1H, J=16.7 Hz), 2.09-2.19 (m, 2H), 2.47 (dd, 2H, J=16.7, 7.9 Hz), 2.59 (ddd, 1H, J=11.7, 8.9, 2.7 Hz), 2.67 (quint, 1H, J=7.4 Hz), 3.52 (brs, 1H), 3.64 (s, 1H), 4.88 (d, 1H, J=10.9 Hz), 4.95 (d, 1H, J=10.9 Hz), 5.28 (m, 1H).

Example 17

Optical resolution of [(1RS,5SR,6SR)-3-ethyl-6-(nitromethyl)bicyclo[3.2.0]hept-3-en-6-yl]acetic acid

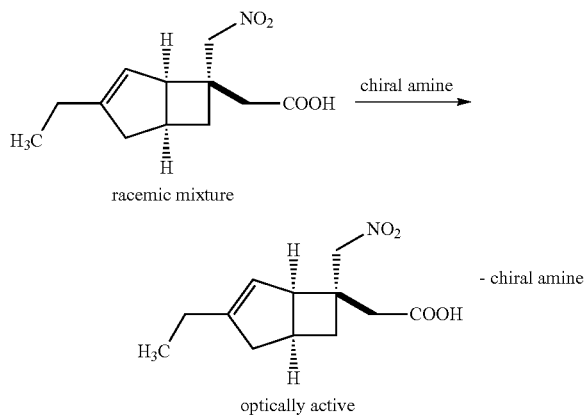

[Formula 41]

[(1RS,5SR,6SR)-3-Ethyl-6-(nitromethyl)bicyclo[3.2.0]hept-3-en-6-yl]acetic acid (0.2 g, 0.84 mmol) was dissolved in CH$_3$CN (3.0 mL). To the solution, each optically active organic amine (0.42 mmol) shown in the table given below was added, and the mixture was stirred at room temperature. The deposited crystals were filtered and dried. Selectivity and yields were determined. The results are shown in the table given below.

TABLE 1

| Entry | Optically active organic amine | Selectivity (% ee) | Yield (%) |
| --- | --- | --- | --- |
| 1 | (1S,2S)-(+)-trans-1-Amino-2-indanol | −83.1* | 14.3 |
| 2 | (R)-(−)-2-Phenylglycinol | −69.2* | 30.7 |
| 3 | Quinine | −62.0* | 44.2 |
| 4 | (R)-(+)-1-(p-Tolyl)ethylamine | 47.6** | 33.1 |

*(1S,5R,6R) - form is main product
**(1R,5S,6S) - form is main product (HPLC Optical Analysis Conditions)

Column: CHIRALPAK AD-RH 4.6×250 mm

Mobile phase: 10 mM phosphate buffer (pH 2.0)/MeCN=25/75 (isocratic)

Flow rate: 1.0 mL/min

Column temperature: 40° C.

Detection wavelength: UV 210 nm

Analysis time: 80 min

Retention time: (1S,5R,6R)-form: 35.2 min, (1R,5S,6S)-form: 42.1 min

Example 18

[(1R,5S,6S)-3-Ethyl-6-(nitromethyl)bicyclo[3.2.0]hept-3-en-6-yl]acetic acid

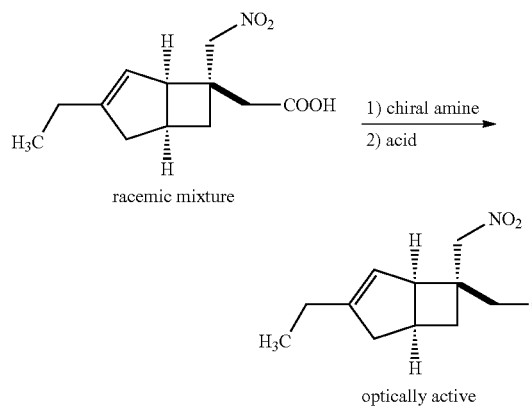

[Formula 42]

racemic mixture optically active

Kinin (5.97 g, 18.4 mmol) was dissolved in acetone (300 mL). To the solution, [(1RS,5SR,6SR)-3-ethyl-6-(nitromethyl)-bicyclo[3.2.0]hept-3-en-6-yl]acetic acid (10.0 g, 33.4 mmol) was added. The mixture was stirred at room temperature for 20 hours, then cooled to 0° C., and stirred for 5 hours. The solid was filtered off and then washed with cold acetone. Then, the filtrate and the washes were concentrated under reduced pressure. To the residue, CH$_3$CN was further added, and the mixture was concentrated again to obtain a concentrated residue (6.4 g, 65.2% ee).

The obtained residue (6.4 g, 65.2% ee) was dissolved in CH$_3$CN (43 mL). To the solution, (S)-(+)-phenylglycinol (1.37 g, 1 equivalent) was added. The mixture was stirred at room temperature for 20 hours, then cooled to 0° C., and stirred for 5 hours. The deposited crystals were collected by filtration and dissolved and separated into aqueous and organic layers by the addition of dilute hydrochloric acid and ethyl acetate. The organic layer was concentrated and then dried under reduced pressure to obtain the title compound (1.39 g, 14%, 92.0% ee).

$^1$H NMR (400 MHz, CDCl$_3$): δ=1.09 (t, 3H, J=7.6 Hz), 1.47-1.57 (m 2H), 2.06-2.17 (m, 3H), 2.27-2.33 (m, 1H), 2.49-2.55 (m, 1H), 2.66 (s, 2H), 2.88 (quint, 1H, J=7.6 Hz), 3.17 (bs, 1H), 4.78 (d, 1H, J=11.5 Hz), 4.86 (d, 1H, J=11.5 Hz), 5.27-5.28 (m, 1H)

Example 19

(1R)-1-Phenylethanaminium [(1R,5S,6S)-3-ethyl-6-(nitromethyl)bicyclo[3.2.0]hept-3-en-6-yl]acetate

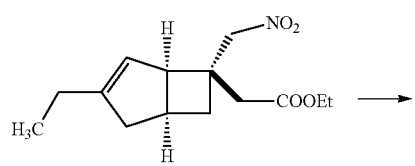

[Formula 43]

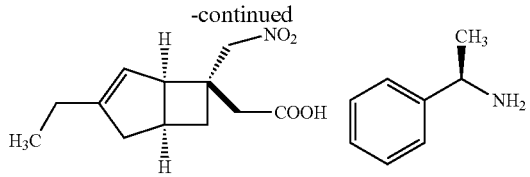

-continued

To ethyl [(1R,5S,6S)-3-ethyl-6-(nitromethyl)bicyclo[3.2.0]hept-3-en-6-yl]acetate (44.5 g (net), 167 mmol, 74% de) obtained by the method shown in Reference Example 1, a 5 mol/L aqueous sodium hydroxide solution (180 mL) was added, and the mixture was stirred at room temperature for 2 hours. To this reaction solution, toluene (300 mL) was added, and the mixture was cooled to 10° C. or lower, followed by the addition of a 30% (w/v) aqueous citric acid solution (600 mL). The aqueous layer was removed, and the organic layer was then washed with water (300 mL). Each aqueous layer was subjected to re-extraction with toluene (300 mL). The organic layers were mixed and concentrated, and MTBE (675 mL) and (R)-phenethylamine (17.6 g, 145 mmol) were then added to the residue. The mixture was stirred at room temperature for approximately 1 hour and then further stirred at 60° C. for 1.5 hours. Then, the reaction mixture was cooled to 0° C. over 1.5 hours and stirred for 1 hour, followed by the filtration of crystals. The crystals were washed with cold MTBE (90 mL) and then dried under reduced pressure at 40° C. to obtain the title compound (49.3 g, 82%, 95.7% de).

$^1$H NMR (500 MHz, CD$_3$OD): δ=1.09 (t, 3H, J=7.4 Hz), 1.49 (dd, 1H, J=12.6, 7.4 Hz), 1.60 (d, 3H, J=6.9 Hz), 2.04 (d, 1H, 16.6 Hz), 2.14 (dd, 2H, J=14.9, 7.4 Hz), 2.28 (ddd, 1H, J=11.5, 9.2, 2.9 Hz), 2.34 (d, 1H, J=16.6 Hz), 2.39 (d, 1H, J=16.6 Hz), 2.48 (dd, 1H, J=16.6, 8.0 Hz), 2.81 (quint, 1H, J=7.4 Hz), 3.22 (bs, 1H), 4.40 (dd, 1H, J=13.7, 6.9 Hz), 4.94 (s, 2H), 5.37 (bs, 1H), 7.36-7.46 (m 5H)

Example 20

Benzylammonium [(1R,5S,6S)-3-ethyl-6-(nitromethyl)bicyclo[3.2.0]hept-3-en-6-yl]acetate

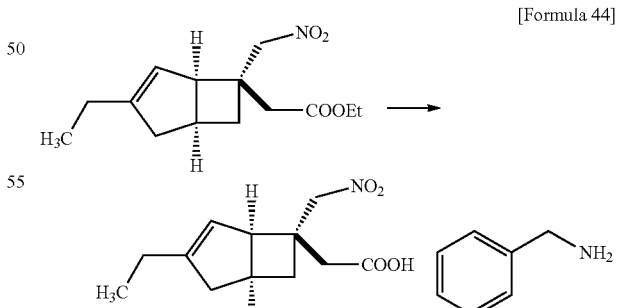

[Formula 44]

To ethyl [(1R,5S,6S)-3-ethyl-6-(nitromethyl)bicyclo[3.2.0]hept-3-en-6-yl]acetate (5.19 g (net), 19.4 mmol, 74% de) obtained by the method shown in Reference Example 1, a 5 mol/L aqueous sodium hydroxide solution (35 mL) was added, and the mixture was stirred at room temperature for 2 hours. This reaction solution was cooled to 0° C., and 6 mol/L hydrochloric acid (32 mL) and ethyl acetate (56 mL) were then added thereto. The aqueous layer was removed, and the organic layer was then washed with saturated saline (14 mL) twice. Each aqueous layer was subjected to re-extraction with ethyl acetate (56 mL). The organic layers were mixed and concentrated, and MTBE (75 mL) and benzylamine (1.6 mL) were then added to the residue. The mixture was stirred overnight at room temperature and then further stirred at 0° C. for 3 hours, followed by the filtration of crystals. The crystals were washed with cold MTBE (14 mL) and then dried under reduced pressure at 40° C. to obtain the title compound (4.01 g, 62%, 98.5% de, 99.8% ee).

$^1$H NMR (500 MHz, CD$_3$OD): δ=1.09 (t, 3H, J=7.4 Hz), 1.49 (dd, 1H, J=12.6, 7.4 Hz), 2.04 (d, 1H, J=16.6 Hz), 2.14 (dd, 2H, J=14.9, 7.4 Hz), 2.28 (ddd, 1H, J=11.5, 9.2, 2.9 Hz), 2.34 (d, 1H, J=16.6 Hz), 2.39 (d, 1H, J=16.6 Hz), 2.48 (dd, 1H, J=16.6, 8.0 Hz), 2.81 (quint, 1H, J=7.4 Hz), 3.22 (bs, 1H), 4.08 (s, 2H), 4.94 (s, 2H), 5.37 (bs, 1H), 7.37-7.46 (m 5H)

Example 21

Ethyl [(1RS,5SR,6SR)-6-cyano-3-ethylbicyclo[3.2.0]hept-3-en-6-yl]acetate (racemate)

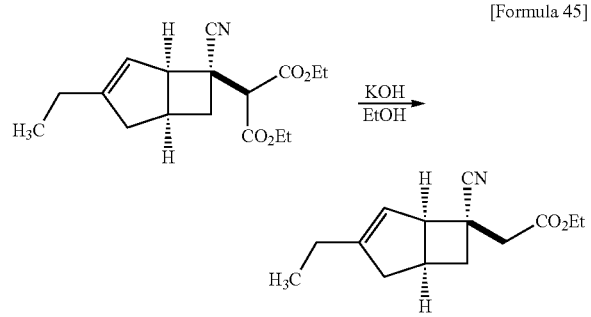

[Formula 45]

Diethyl [(1RS,5SR,6RS)-6-cyano-3-ethylbicyclo[3.2.0]hept-3-en-6-yl]propanedioate (63.9 mg, 0.209 mmol) was dissolved in EtOH (0.8 mL). To the solution, a 2.0 M solution of potassium hydroxide in EtOH (210 μL, 0.420 mmol) was added. The mixture was stirred under heating at 70° C. for 6 hours, and the reaction was then terminated by the addition of 1 M hydrochloric acid (5 mL), followed by extraction with DCM (5 mL) three times. The solvent was distilled off under reduced pressure, and the residue was then purified by PTLC (hexane:ethyl acetate=5:1) to obtain the title compound as a clear colorless oil (10.0 mg, 21%).

$^1$H NMR (CDCl$_3$) (400 MHz): δ=1.08 (3H, t, J=7.6 Hz), 1.28 (3H, t, J=7.2 Hz), 1.73 (1H, dd, J=12.2, 7.6 Hz), 2.05 (1H, d, J=16.8 Hz), 2.14 (2H, q, J=7.6 Hz), 2.52 (1H, dd, J=16.6, 7.6 Hz), 2.61 (2H, s), 2.66-2.79 (1H, m), 3.14 (1H, quint, J=7.6 Hz), 3.65-3.77 (1H, m), 4.18 (2H, q, J=7.2 Hz), 5.25 (1H, s).

$^{13}$C NMR (CDCl$_3$) (100 MHz): δ=12.3, 14.1, 24.4, 32.3, 36.2, 38.1, 38.6, 42.5, 54.5, 61.0, 119.2, 125.0, 152.8, 169.6.

Example 22

[(1RS,5SR,6SR)-6-Cyano-3-ethylbicyclo[3.2.0]hept-3-en-6-yl]acetic acid and [(1RS,5SR,6RS)-6-cyano-3-ethylbicyclo[3.2.0]hept-3-en-6-yl]propanedioic acid (racemate)

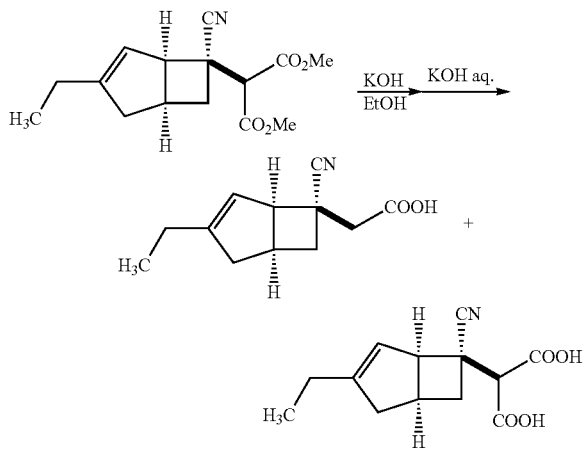

[Formula 46]

Dimethyl [(1RS,5SR,6RS)-6-cyano-3-ethylbicyclo[3.2.0]hept-3-en-6-yl]propanedioate (502.5 mg, 1.81 mmol) was dissolved in EtOH (1.0 mL). To the solution, a 1.5 M solution of potassium hydroxide in EtOH (1.21 mL, 1.82 mmol) was added, and the mixture was heated to reflux for 4 hours. After cooling to room temperature, a 2 M aqueous potassium hydroxide solution (1.81 mL) was added thereto, and the mixture was stirred at room temperature for 3 hours. EtOH was distilled off under reduced pressure, followed by extraction with DCM (5 mL) and then extraction with a 1 M aqueous sodium hydroxide solution. The obtained aqueous layer was neutralized until acidic by the addition of concentrated hydrochloric acid, followed by extraction with DCM (5 mL) three times. The solvent was distilled off under reduced pressure to obtain a product as a yellow oil (350.6 mg). The product was confirmed by $^1$H NMR and HPLC to be a mixture of [(1RS,5SR,6SR)-6-cyano-3-ethylbicyclo[3.2.0]hept-3-en-6-yl]acetic acid and [(1RS,5SR,6RS)-6-cyano-3-ethylbicyclo[3.2.0]hept-3-en-6-yl]propanedioic acid (84:16).

[(1RS,5SR,6SR)-6-Cyano-3-ethylbicyclo[3.2.0]hept-3-en-6-yl]acetic acid $^1$H NMR (CDCl$_3$) (400 MHz): δ=1.07 (3H, t, J=7.6 Hz), 1.73 (1H, dd, J=12.6, 7.6 Hz), 2.05 (1H, d, J=17.2 Hz), 2.14 (2H, q, J=7.2 Hz), 2.52 (1H, dd, J=16.8, 7.6 Hz), 2.69 (2H, s), 2.69-2.80 (1H, m), 3.15 (1H, quint, J=7.6 Hz), 3.65-3.79 (1H, m), 5.27 (1H, s), 11.17 (1H, brs).

[(1RS,5SR,6RS)-6-Cyano-3-ethylbicyclo[3.2.0]hept-3-en-6-yl]propanedioic acid $^1$H NMR (CDCl$_3$) (400 MHz): δ=1.08 (3H, t, J=7.6 Hz), 1.86 (1H, dd, J=12.6, 8.0 Hz), 2.00-2.23 (3H, m), 2.53 (1H, dd, J=16.8, 7.6 Hz), 2.66-2.83 (1H, m), 3.17 (1H, quint, J=7.6 Hz), 3.73 (1H, s), 3.73-3.82 (1H, m), 5.31 (1H, s), 11.57 (2H, brs).

Example 23

Cyclohexylammonium [(1R,5S,6S)-6-cyano-3-ethyl-bicyclo[3.2.0]hept-3-en-6-yl]acetate

[Formula 47]

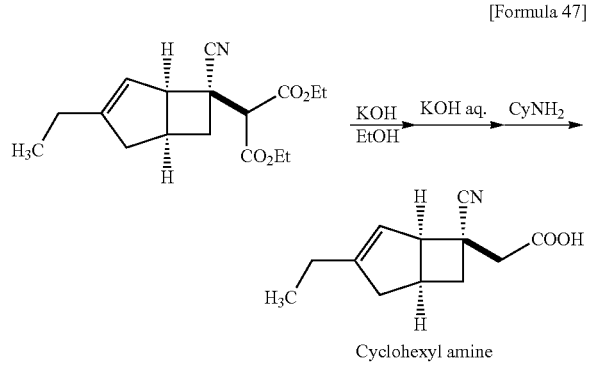

Cyclohexyl amine

Diethyl [(1R,5S,6R)-6-cyano-3-ethylbicyclo[3.2.0]hept-3-en-6-yl]propanedioate (34.16 g, 103.7 mmol) was dissolved in EtOH (95 mL). To the solution, a 0.5 M solution of potassium hydroxide in EtOH (275 mL, 138 mmol) was added dropwise over 8 hours under heating to reflux. After cooling to room temperature, insoluble matter was filtered and washed with EtOH (95 mL). To the obtained solution, a 1 M aqueous potassium hydroxide solution (95 mL) was added, and the mixture was stirred at room temperature for 20 hours. Approximately 480 mL of EtOH was distilled off under reduced pressure. After addition of water (160 mL), the mixture was washed with toluene (160 mL). To the obtained aqueous layer, toluene (160 mL) and concentrated hydrochloric acid (20 mL) were added at 0° C. for separation into aqueous and organic layers and extraction. The aqueous layer was subjected to re-extraction by the addition of toluene (160 mL). The organic layers were combined and washed with saturated saline (160 mL), and the solvent was then distilled off under reduced pressure. The obtained oil (22.92 g) was dissolved in toluene (470 mL). To the solution, CyNH$_2$ (10.29 g, 103.7 mmol) was added. The mixture was stirred overnight at room temperature, and the resulting crystals were then filtered, washed with toluene (80 mL), and dried in vacuum at 40° C. to obtain the title compound (28.89 g, 92%, 97.4% ee).

$^1$H NMR (CDCl$_3$) (400 MHz): δ=1.06 (3H, t, J=7.6 Hz), 1.08-1.47 (6H, m), 1.62 (1H, d, J=12.0 Hz), 1.69 (1H, dd, J=12.6, 7.6 Hz), 1.69-1.86 (2H, m), 1.93-2.20 (5H, m), 2.45 (2H, s), 2.39-2.56 (1H, m), 2.66 (1H, ddd, J=13.7, 9.0, 2.4 Hz), 2.92-3.16 (2H, m), 3.57-3.72 (1H, m), 5.28 (1H, s), 7.30 (2H, brs).

(Optical Purity Measurement Method)
Column: CHIRALPAK AS-RH (Daicel, 5 μm, 4.6 mm×150 mm), 40° C.
Detection wavelength: UV 210 nm
Mobile phase: MeCN:10 mM phosphate buffer solution (prepared at pH 2 with phosphate)=22:78
Measurement time: 30 min
Flow rate: 1.0 mL/min Retention time:
[(1R,5S,6S)-6-Cyano-3-ethylbicyclo[3.2.0]hept-3-en-6-yl] acetic acid: 21.8 min
[(1S,5R,6R)-6-Cyano-3-ethylbicyclo[3.2.0]hept-3-en-6-yl] acetic acid: 19.1 min

Example 24

(1R)-1-Phenylethanaminium [(1R,5S,6S)-6-cyano-3-ethylbicyclo[3.2.0]hept-3-en-6-yl]acetate

[Formula 48]

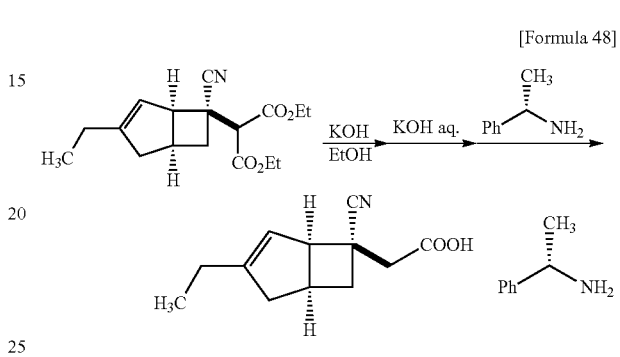

Diethyl [(1R,5S,6R)-6-cyano-3-ethylbicyclo[3.2.0]hept-3-en-6-yl]propanedioate (1.309 g, 4.153 mmol, 97.4% ee) was dissolved in EtOH (3.9 mL). To the solution, a 0.5 M solution of potassium hydroxide in EtOH (10.8 mL, 5.40 mmol) was added dropwise over 7.5 hours under heating to reflux. After cooling to room temperature, insoluble matter was filtered and washed with EtOH (4 mL). To the obtained solution, a 1 M aqueous potassium hydroxide solution (4.0 mL) was added, and the mixture was stirred at room temperature for 2 hours.

EtOH was distilled off under reduced pressure, and the residue was washed with toluene (8 mL). To the obtained aqueous layer, toluene (8 mL) and concentrated hydrochloric acid (1 mL) were added at 0° C. for separation into aqueous and organic layers and extraction. The aqueous layer was subjected to re-extraction by the addition of toluene (8 mL). The organic layers were combined and washed with saturated saline (8 mL). Then, 15.8124 g of the obtained solution (31.6992 g) was used in the subsequent procedures. The solvent was distilled off under reduced pressure, and the obtained oil was dissolved in CH$_3$CN (15 mL). To the solution, (R)-phenethylamine (264 μL, 2.07 mmol) was added. The mixture was stirred overnight at room temperature and then cooled to 0° C., and the resulting crystals were filtered, washed with CH$_3$CN (5 mL), and dried in vacuum at 40° C. to obtain the title compound (520.6 mg, 77%, 98.2% ee).

Example 25 tert-Butylammonium [(1R,5S,6S)-6-cyano-3-ethyl-bicyclo[3.2.0]hept-3-en-6-yl]acetate

[Formula 49]

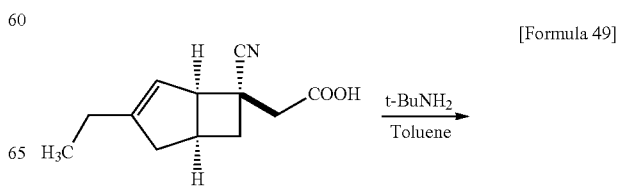

-continued

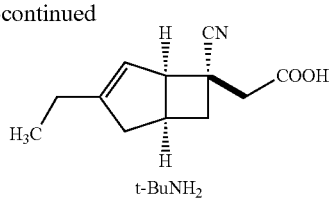

t-BuNH₂

To a solution of [(1R,5S,6S)-6-cyano-3-ethylbicyclo[3.2.0]hept-3-en-6-yl]acetic acid (100 mg, 0.487 mmol, 90% ee) in toluene (1 mL), t-butylamine (52 μL, 0.495 mmol) was added, and the mixture was stirred overnight at room temperature. The resulting crystals were filtered to obtain the title compound (64.9%, 97.8% ee).

Example 26

Benzylammonium [(1R,5S,6S)-6-cyano-3-ethylbicyclo[3.2.0]hept-3-en-6-yl]acetate

[Formula 50]

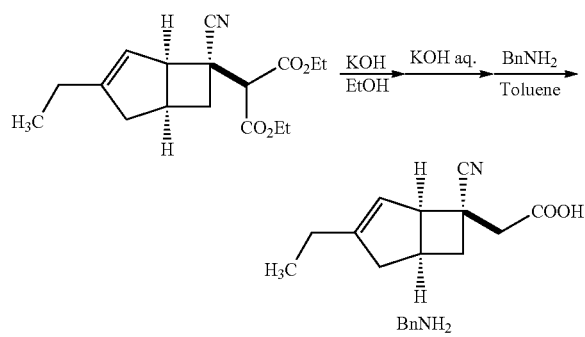

BnNH₂

A solution of diethyl [(1R,5S,6R)-6-cyano-3-ethylbicyclo[3.2.0]hept-3-en-6-yl]propanedioate (22.0 mmol) in EtOH (16 vol.) was heated to reflux, and an 8 M aqueous potassium hydroxide solution (3.44 mL) was added thereto every 1 hour in 5 portions. Then, the mixture was heated to reflux for 8 hours and cooled to room temperature. Then, an 8 M aqueous potassium hydroxide solution (2.1 mL) was added thereto, and the mixture was stirred at room temperature for 1 hour. The solvent was concentrated into 18 mL under reduced pressure, and water (18 mL) and toluene (18 mL) were added to the residue. The mixture was cooled to 0° C. and then neutralized until pH 2.5 by the addition of concentrated hydrochloric acid (4.56 g), followed by separation into aqueous and organic layers and extraction. To the obtained organic layer, toluene (24 mL) was added, and the mixture was cooled to 10° C. or lower, followed by the addition of benzylamine (2.36 g). The solvent was concentrated into 18 mL under reduced pressure. Then, toluene (12 mL) was added to the residue, and the mixture was stirred overnight at room temperature. The resulting crystals were filtered, washed with toluene (15 mL), and then dried in vacuum at 40° C. to obtain the title compound (5.27 g, 76.6%, 98.6% ee).

¹H NMR (CD₃OD) (400 MHz): δ=1.09 (3H, t, J=7.6 Hz), 1.73 (1H, dd, J=12.2, 8.0 Hz), 2.07 (1H, d, J=16.8 Hz), 2.15 (2H, q, J=7.6 Hz), 2.41-2.55 (3H, m), 2.58-2.67 (1H, m), 3.06 (1H, quint, J=7.6 Hz), 3.57-3.62 (1H, m), 4.09 (2H, s), 5.36 (1H, s), 7.28-7.50 (5H, m).

Example 27

Benzylammonium [(1R,5S,6S)-6-cyano-3-ethylbicyclo[3.2.0]hept-3-en-6-yl]acetate

[Formula 51]

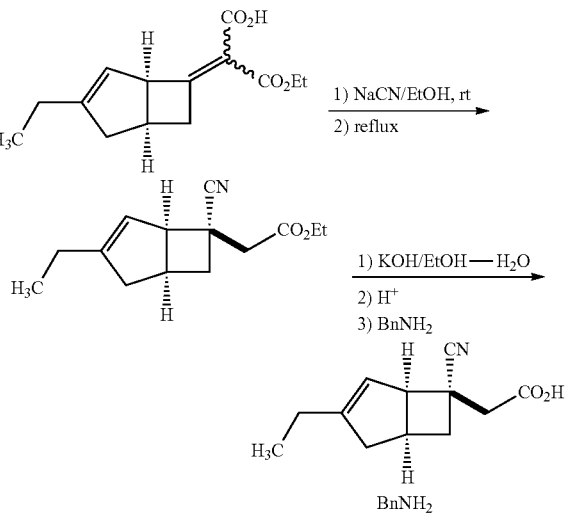

BnNH₂

To the crude product of (2EZ)-3-ethoxy-2-[(1R,5S)-3-ethylbicyclo[3.2.0]hept-3-en-6-ylidene]-3-oxopropanoic acid (4.7 g) obtained by the method shown in Example 1, EtOH (30 mL) and sodium cyanide (1.4 g, 14.54 mmol) were added, and the mixture was stirred at 25° C. for 46 hours and then refluxed for 5 hours. A 1 N aqueous potassium hydroxide solution (21.8 mL) was added thereto, and the mixture was stirred at room temperature for 2 hours. The solvent was distilled off by concentration under reduced pressure. Water (12 mL) and toluene (8 mL) were added to the residue for separation into aqueous and organic layers, and the organic layer was removed. Then, toluene (10 mL) was added to the aqueous layer, and the mixture was cooled and adjusted to pH 2.5 by the addition of 6 N hydrochloric acid. After separation into aqueous and organic layers, the aqueous layer was removed, and the solvent was distilled off by concentration under reduced pressure. Then, toluene (16 mL) and benzylamine (1.6 g, 14.54 mmol) were added to the residue. After mixing at room temperature for 5 hours, the crystals were filtered. Then, the crystals were dried under reduced pressure at 40° C. to obtain the title compound as white crystals (2.8 g, 58.9%).

Example 28

Benzylammonium [(1R,5S,6S)-6-cyano-3-ethylbicyclo[3.2.0]hept-3-en-6-yl]acetate

[Formula 52]

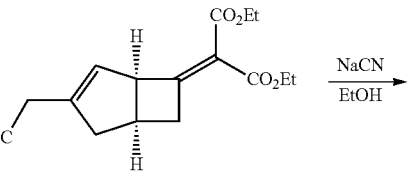

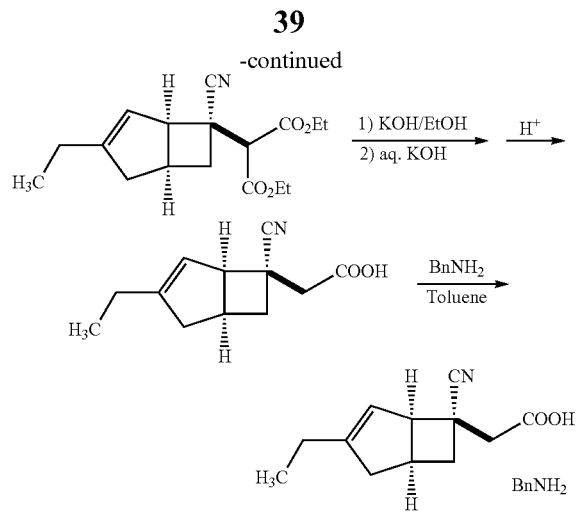

To a CPME solution of diethyl [(1RS,5SR,6RS)-6-cyano-3-ethylbicyclo[3.2.0]hept-3-en-6-yl]propanedioate obtained by the method of Example 12, EtOH (390 mL) was added, then an 8 N aqueous potassium hydroxide solution (6.9 mL, 55.07 mmol) was added a total of 5 times every 1 hour under heating to reflux, and the mixture was then refluxed for 5 hours and brought back to room temperature.

To the EtOH solution, water (60 mL) and an 8 N aqueous potassium hydroxide solution (24 mL) were added, and the mixture was stirred at 26 to 27° C. for 2 hours and then concentrated into 150 mL under reduced pressure at an external temperature of 40 to 45° C. To the residue, water (180 mL) and toluene (90 mL) were added for separation into aqueous and organic layers, and the organic layer was removed.

To the obtained aqueous solution, toluene (150 mL) was added, and the mixture was cooled and adjusted to pH 1.4 by the addition of concentrated hydrochloric acid (42.5 mL) at 2 to 9° C. After separation into aqueous and organic layers, the aqueous layer was removed, and toluene (300 mL) and benzylamine (23.6 g, 220.28 mmol) were added to the residue. After inoculation, the mixture was stirred at 44 to 46° C. for 30 minutes and then concentrated into 300 mL under reduced pressure at 44 to 46° C. After stirring overnight at 22 to 23° C., the crystals were filtered. The crystals were dried under reduced pressure at 40° C. to obtain the title compound as white crystals (54.4 g, 79.2% from (1R,5S)-3-ethylbicyclo[3.2.0]hept-3-en-6-one).

Example 29

[(1R,5S,6S)-6-(Aminomethyl)-3-ethylbicyclo[3.2.0]hept-3-en-6-yl]acetic acid

[Formula 53]

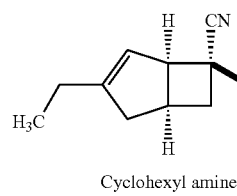

HCl aq.
Toluene

H$_2$
Sponge Ni
───────→
KOH aq.
NH$_3$ aq.

Cyclohexyl amine

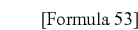

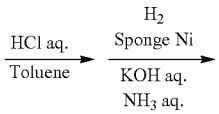

Cyclohexylammonium [(1R,5S,6S)-6-cyano-3-ethylbicyclo[3.2.0]hept-3-en-6-yl]acetate (6.00 g, 19.7 mmol) was dissolved in toluene (30 mL) and 1 M hydrochloric acid (30 mL) for separation into aqueous and organic layers and extraction. The obtained organic layer was washed with saturated saline (30 mL), and the solvent was then distilled off under reduced pressure to obtain [(1R,5S,6S)-6-cyano-3-ethylbicyclo[3.2.0]hept-3-en-6-yl]acetic acid as a red-brown oil (4.86 g). An 8 M aqueous potassium hydroxide solution (3.7 mL, 29.6 mmol), 28% ammonia water (16.6 mL), and sponge nickel (Kawaken NDHT-M3, 2.05 g) were added thereto, and the mixture was stirred under heating at 40° C. for 15 hours at a hydrogen pressure of 4 bar. After cooling to room temperature, nitrogen substitution was performed, and the sponge nickel was filtered and washed with a 1 M aqueous potassium hydroxide solution (9 mL). To 16.51 g (corresponding to 9.83 mmol of cyclohexylammonium [(1R,5S,6S)-6-cyano-3-ethylbicyclo[3.2.0]hept-3-en-6-yl]acetate) of the obtained solution (33.08 g), active carbon (Purified Shirasagi, 0.300 g) was added, and the mixture was stirred at room temperature for 4 hours. The active carbon was filtered and washed with a 1 M aqueous potassium hydroxide solution (4.0 mL). Then, the obtained solution was cooled to 0° C., adjusted to pH 6.6 by the addition of concentrated hydrochloric acid (3.2 mL), and stirred. The resulting crystals were filtered, washed with water (4.0 mL), and then dried in vacuum at 50° C. to obtain the title compound as white crystals (1.72 g, 77%).

Various spectral data of the obtained title compound were almost (structurally identifiably) consistent with public information (described in Patent Literatures 5 and 6).

Example 30

Di-tert-butyl [(1RS,5SR,6RS)-6-(aminomethyl)-3-ethylbicyclo[3.2.0]hept-3-en-6-yl]propanedioate benzenesulfonate (racemate)

[Formula 54]

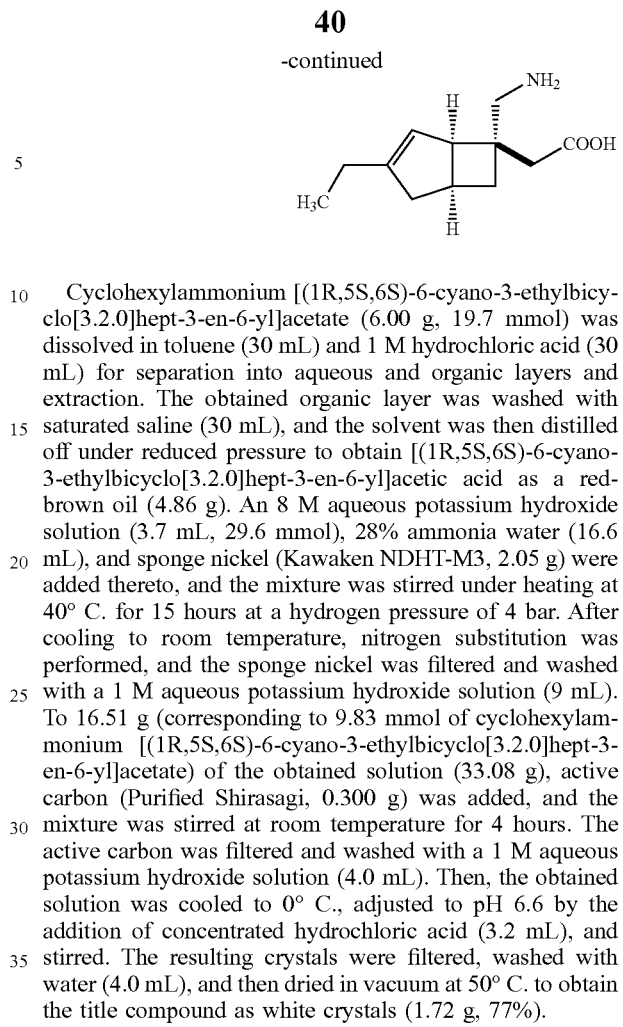

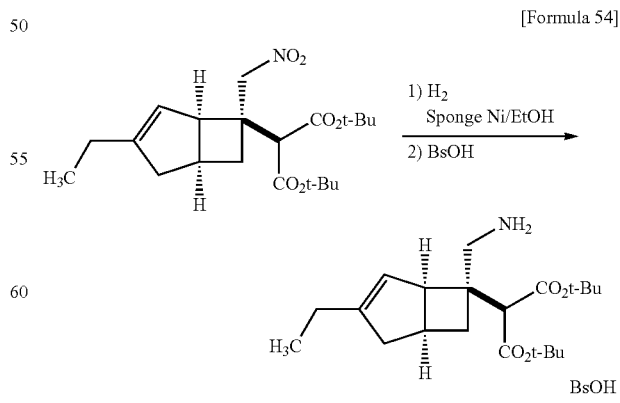

To di-tert-butyl [(1RS,5SR,6RS)-3-ethyl-6-(nitromethyl)bicyclo[3.2.0]hept-3-en-6-yl]propanedioate (20.6 g), EtOH (85 mL) and sponge nickel (6.18 g) were added, and the mixture was heated to 35° C. under application of hydrogen gas pressure (0.45 MPa) and stirred for 10 hours. Then, the reaction solution was cooled to room temperature and filtered to remove the sponge nickel. The sponge nickel on the filter was washed with EtOH (60 mL), and the washes were combined with the reaction solution.

After concentration of this solution, toluene (170 mL) was added to the residue, and the mixture was further concentrated. To the residue, diisopropyl ether (100 mL) and BsOH (7.35 g) were added, and the mixture was stirred at room temperature for approximately 2 hours, followed by the addition of heptane (100 mL). The mixture was stirred at room temperature for 1 hour, then cooled to 0° C., and further stirred for 1 hour. The deposited crystals were filtered and dried to obtain the title compound (17.36 g, 64%).

$^1$H NMR (CDCl$_3$) (500 MHz): δ=1.07 (t, 3H, J=7.4 Hz), 1.40 (s, 9H), 1.44 (s, 9H), 1.95 (d, 1H, J=16.6 Hz), 2.05-2.17 (m, 3H), 2.25 (ddd, 1H, J=11.5, 8.0, 2.3 Hz), 2.39 (dd, 1H, J=16.6, 7.4 Hz), 2.84 (quint, 1H, J=7.4 Hz), 3.20 (brs, 1H), 3.36 (d, 1H, J=11.5 Hz), 3.37 (d, 1H, J=11.5 Hz), 3.67 (s, 1H), 5.18 (brs, 1H), 7.33-7.38 (m, 3H), 7.89-7.93 (m, 2H), 8.27 (s, 3H).

Example 31

[(1R,5S,6S)-6-(Aminomethyl)-3-ethylbicyclo[3.2.0]hept-3-en-6-yl]acetic acid

[Formula 55]

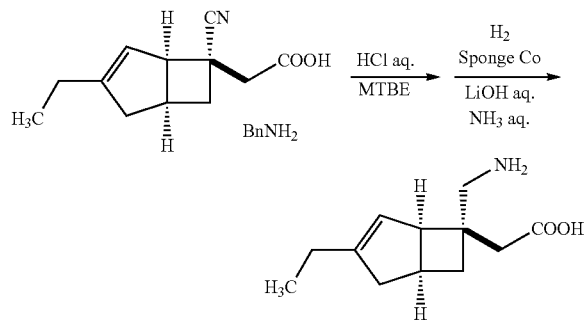

Benzylammonium [(1R,5S,6S)-6-cyano-3-ethylbicyclo[3.2.0]hept-3-en-6-yl]acetate (60 g) was dissolved by the addition of MTBE (300 mL), water (127 mL), and concentrated hydrochloric acid (23 mL) at room temperature. The solution was left standing, and the aqueous layer was removed to obtain an organic layer. A 1.75 mol/L aqueous lithium hydroxide solution (approximately 336 mL) was added thereto until the pH of the reaction solution became 10.0. The mixture was left standing, and the organic layer was then removed. To the obtained aqueous solution, sponge cobalt (16 g), 25% ammonia water (21.6 mL), and a 20% solution of dimethylpolysiloxane in MTBE (0.3 mL) were added, and the mixture was heated to 40° C. under application of hydrogen gas pressure (0.45 MPa) and stirred for 7.5 hours. Then, the reaction solution was cooled to room temperature and filtered to remove the sponge cobalt. The sponge cobalt on the filter was washed with purified water (90 mL).

To the obtained solution, active carbon (1.5 g) was added, and the mixture was stirred for 0.5 hours and filtered to remove the active carbon. The active carbon on the filter was washed with water (90 mL). This solution was cooled to approximately 0° C. and adjusted to approximately pH 6.0 by the dropwise addition of a 50% aqueous malonic acid solution (approximately 42 mL) over 2.5 hours. The resulting crystals were filtered, washed with water (120 mL) cooled to approximately 0° C., and dried in vacuum overnight at 50° C. to obtain the title solid as white crystals (36.19 g, 90.0%). Various spectral data of the obtained title compound were almost (structurally identifiably) consistent with public information (described in Patent Literatures 5 and 6).

Example 32

[(1R,5S,6S)-6-(Aminomethyl)-3-ethylbicyclo[3.2.0]hept-3-en-6-yl]acetic acid

[Formula 56]

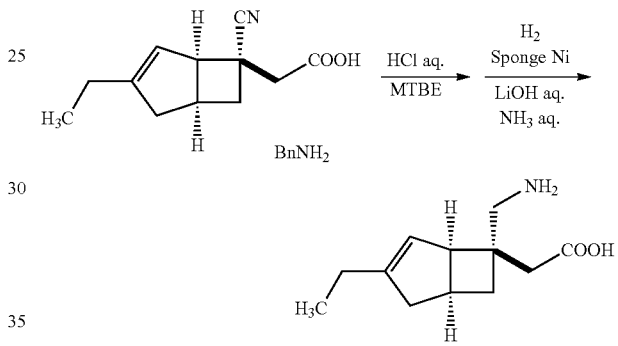

Benzylammonium [(1R,5S,6S)-6-cyano-3-ethylbicyclo[3.2.0]hept-3-en-6-yl]acetate (5.0 g) was dissolved by the addition of MTBE (25 mL), water (10 mL), and concentrated hydrochloric acid (1.94 mL) at room temperature. The solution was left standing, and the aqueous layer was removed to obtain an organic layer. A 4 mol/L aqueous lithium hydroxide solution (approximately 6.0 mL) and water (3 mL) were added thereto. The mixture was stirred and left standing, and the organic layer was then removed. To the obtained aqueous solution, sponge nickel (1.25 g), 25% ammonia water (3.6 mL), and a 20% solution of dimethylpolysiloxane in MTBE (0.025 mL) were added, and the mixture was heated to 40° C. under application of hydrogen gas pressure (0.45 MPa) and stirred for 4 hours. Then, the reaction solution was cooled to room temperature and filtered to remove the sponge nickel. The sponge nickel on the filter was washed with water (7.5 mL).

To the obtained solution, active carbon (0.125 g) was added, and the mixture was stirred for 0.5 hours and filtered to remove the active carbon. The active carbon on the filter was washed with water (7.5 mL). This solution was cooled to approximately 0° C. and adjusted to approximately pH 6.0 by the dropwise addition of a 50% aqueous citric acid solution (approximately 7.5 mL) over 3 hours. The resulting crystals were filtered, washed with water (10 mL) cooled to approximately 0° C., and dried in vacuum overnight at 50° C. to obtain the title compound as white crystals (2.90 g, 86.6%).

Example 33

[(1R,5S,6S)-6-(Aminomethyl)-3-ethylbicyclo[3.2.0]hept-3-en-6-yl]acetic acid

[Formula 57]

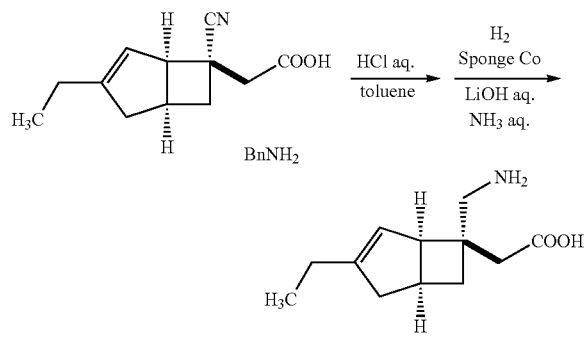

Benzylammonium [(1R,5S,6S)-6-cyano-3-ethylbicyclo[3.2.0]hept-3-en-6-yl]acetate (40.0 g) was dissolved by the addition of toluene (200 mL) and 2 mol/L hydrochloric acid (100 mL) at room temperature. The solution was left standing, and the aqueous layer was removed to obtain an organic layer. 10% saline (approximately 100 mL) was added thereto. The mixture was stirred and left standing, and the aqueous layer was then removed. To this solution, water (100 mL) was added, and the mixture was then adjusted to pH 10.0 by the addition of an 8 mol/L aqueous potassium hydroxide solution (approximately 15.7 mL) and left standing. Then, the organic layer was removed.

To this solution, sponge cobalt (10 g), 28% ammonia water (13 mL), and a 2% solution of dimethylpolysiloxane in toluene (2 mL) were added, and the mixture was heated to 40° C. under application of hydrogen gas pressure (0.45 MPa) and stirred for 8 hours. Then, the reaction solution was cooled to room temperature and filtered to remove the sponge cobalt. The sponge cobalt on the filter was washed with water (80 mL). To the obtained solution, active carbon (4 g) was added, and the mixture was stirred for 0.5 hours and filtered to remove the active carbon. The active carbon on the filter was washed with water (60 mL). This solution was adjusted to approximately pH 6.0 by the addition of concentrated hydrochloric acid (approximately 32.7 g). Then, potassium chloride (55.0 g) was added thereto, and the mixture was stirred for 0.5 hours and then cooled to 0° C. The resulting crystals were filtered, washed with 20% saline (80 mL) cooled to approximately 0° C., and dried in vacuum overnight at 50° C. to obtain the title compound as white crystals (26.9 g, content: 88.3%, content-based yield: 88.7%).

Example 34

[(1R,5S,6S)-6-(Aminomethyl)-3-ethylbicyclo[3.2.0]hept-3-en-6-yl]acetic acid

[Formula 58]

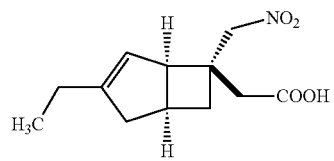

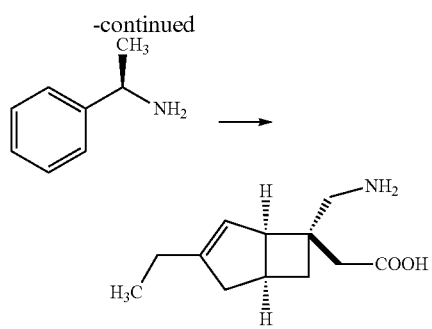

To (R)-phenylethanaminium [(1R,5S,6S)-6-cyano-3-ethylbicyclo[3.2.0]hept-3-en-6-yl]acetate (35.9 g, 99.2 mmol, 95.7% de, 99.2% ee), toluene (120 mL) and 1 mol/L hydrochloric acid (150 mL) were added, and the mixture was stirred. The aqueous layer was removed, and the organic layer was then washed with water (120 mL) twice and concentrated. To the obtained residue, MTBE (150 mL) and sponge nickel (10.1 g) were added, and the mixture was stirred at room temperature for 3 hours under application of hydrogen pressure (approximately 4 atm). To this reaction solution, a 2 mol/L aqueous potassium hydroxide solution (72 mL) was added, and the mixture was stirred for 30 minutes. Then, the sponge nickel was filtered off. The filtered sponge nickel was washed with a 2 mol/L aqueous potassium hydroxide solution (12 mL). The filtrate and the washes were combined, and the organic layer was then removed to obtain an aqueous layer. The organic layer was subjected to re-extraction with a 2 M aqueous potassium hydroxide solution. Combined aqueous layers were cooled, adjusted to pH 7.5 by the addition of concentrated hydrochloric acid (approximately 12 mL), and then stirred at 0° C. for approximately 3 hours. The deposited crystals were filtered, washed with ice-cold water (24 mL), and then dried under reduced pressure at 50° C. to obtain the title compound (18.3 g, 88%, 99.8% de).

Example 35

[(1R,5S,6S)-6-(Aminomethyl)-3-ethylbicyclo[3.2.0]hept-3-en-6-yl]acetic acid monobenzenesulfonate

[Formula 59]

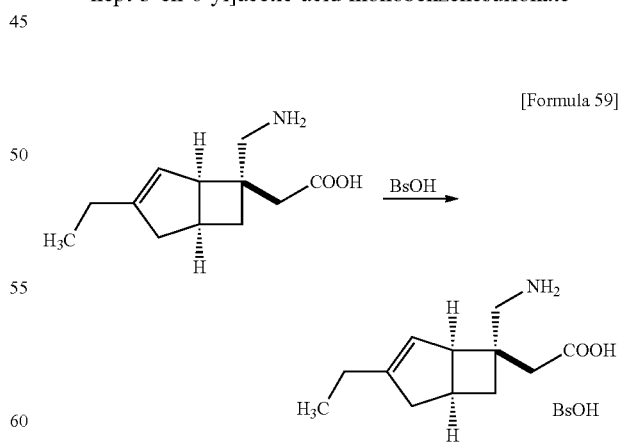

To a mixed solution of MTBE (83 mL), acetone (4.0 mL), and water (0.98 mL), [(1R,5S,6S)-6-(aminomethyl)-3-ethylbicyclo[3.2.0]hept-3-en-6-yl]acetic acid (4.07 g, 19.5 mmol) was added at 0° C., and the mixture was stirred to prepare a slurry. A solution of BsOH (3.08 g, 19.5 mmol) in acetone (10.1 mL) was added thereto. The mixture was stirred at 0° C. for 1 hour, then heated to room temperature, and stirred for 2 hours. The reaction mixture was slowly cooled to −10° C. over 1 hour and stirred for 2.5 hours. The resulting crystals were filtered, washed with acetone (12 mL) cooled to 0° C., and then dried in vacuum at 40° C. to obtain the title compound as white crystals (6.44 g, 90.1%). Various spectral data of the obtained title compound were almost (structurally identifiably) consistent with public information (described in Patent Literatures 5 and 6).

(Purity Measurement Method-1)

Column: Cadenza CW-C18 (Imtakt, 3 μm, 4.6 mm×150 mm), 40° C.

Detection wavelength: UV 205 nm

Mobile phase: MeCN:5 mM aqueous ammonium bicarbonate solution=10:90-80:20 (gradient)

(0-12 min: MeCN 10%, 12-27 min: MeCN 10→80%, 27-45 min: MeCN 80%, 45-50 min: MeCN 80→10%, 50-60 min: MeCN 10%, 60 min: STOP)

Measurement time: 60 min

Flow rate: 1.0 mL/min

Concentration of injected sample: 5 mg/mL

Amount of sample injected: 2 μL

Retention time:

Title compound (in terms of free form): 12.5 min

Diastereomer (compound X): 13.5 min

Positional isomers of double bond (compound XII or XIII): 9.4 min, 9.6 min, 11.4 min (Purity Measurement Method-2)

Column: TSKgel ODS-100V (Tosoh, 3 μm, 4.6 mm×150 mm), 40° C.

Detection wavelength: UV 215 nm

Mobile phase: MeCN:10 mM phosphate buffer solution (pH 6.4)/MeCN mixed solution (2:8)=0:100-94:6 (gradient)

(0-40 min: MeCN 0→55%, 40-40.1 min: MeCN 55→94%, 40.1-50 min: MeCN 94%, 50 min: STOP)

Measurement time: 50 min

Flow rate: 1.0 mL/min

Concentration of injected sample: 5 mg/mL

Amount of sample injected: 10 μL

Retention time:

Title compound (in terms of free form): 22.6 min

Diastereomer (compound X): 22.9 min

Positional isomers of double bond (compound XII or XIII): 21.3 min, 21.4 min, 22.2 min Example 36

[(1R,5S,6S)-6-(Aminomethyl)-3-ethylbicyclo[3.2.0]hept-3-en-6-yl]acetic acid monobenzenesulfonate

[Formula 60]

To a solution of BsOH (5.29 g) in water (35 mL), [(1R,5S,6S)-6-(aminomethyl)-3-ethylbicyclo[3.2.0]hept-3-en-6-yl]acetic acid (7.00 g) was added at approximately 25° C., and the mixture was heated to approximately 50° C. After confirmation of the dissolution of crystals, the mixture was cooled to approximately 0° C. over 2.5 hours. The crystals were filtered, washed with cold water (21 mL), and then dried in vacuum at 55° C. to obtain the title compound as white crystals (10.50 g, 85.4%).

Example 37

[(1R,5S,6S)-6-(Aminomethyl)-3-ethylbicyclo[3.2.0]hept-3-en-6-yl]acetic acid monobenzenesulfonate

[Formula 61]

To [(1R,5S,6S)-6-(aminomethyl)-3-ethylbicyclo[3.2.0]hept-3-en-6-yl]acetic acid (13.00 g), CH$_3$CN (195 mL) and water (2.6 mL) were added, and the temperature of the mixture was adjusted to approximately 20° C. Then, a solution of BsOH (9.83 g) in CH$_3$CN (39 mL) was added dropwise thereto over approximately 20 minutes. After addition of CH$_3$CN (23.4 mL), the mixture was cooled to approximately 0° C. over 2 hours. The crystals were filtered, washed with cold CH$_3$CN (39 mL), and then dried in vacuum at 55° C. to obtain the title compound as white crystals (21.64 g, 94.8%).

Example 38

[(1R,5S,6S)-6-(Aminomethyl)-3-ethylbicyclo[3.2.0]hept-3-en-6-yl]acetic acid monobenzenesulfonate

[Formula 62]

To [(1R,5S,6S)-6-(aminomethyl)-3-ethylbicyclo[3.2.0]hept-3-en-6-yl]acetic acid (13.00 g), anisole (130 mL) was added, and the temperature of the mixture was adjusted to 20 to 25° C. Then, a solution of BsOH (9.83 g) in anisole (26 mL) was added dropwise thereto over 27 minutes. After addition of anisole (26 mL), the mixture was stirred at 20 to 25° C. for 2 hours and cooled to 3° C. over 2 hours. The crystals were filtered, washed with acetone (39 mL) cooled to 0° C., and then dried in vacuum at 55° C. to obtain the title compound as white crystals (21.88 g, 95.9%).

Example 39

[(1R,5S,6S)-6-(Aminomethyl)-3-ethylbicyclo[3.2.0]hept-3-en-6-yl]acetic acid monobenzenesulfonate

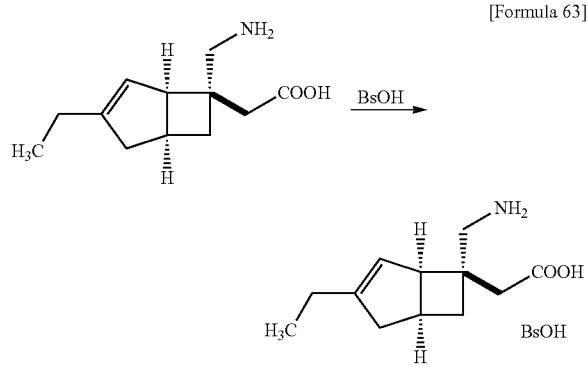

[Formula 63]

To [(1R,5S,6S)-6-(aminomethyl)-3-ethylbicyclo[3.2.0]hept-3-en-6-yl]acetic acid (13.00 g), anisole (130 mL) was added, and the temperature of the mixture was adjusted to 20 to 25° C. Then, acetic acid (10.66 mL) was added thereto, and insoluble matter was filtered and washed with a 3% solution of acetic acid in anisole (10.66 mL). To the obtained solution, a solution of BsOH (9.83 g) in anisole (26 mL) was added dropwise over 40 minutes. After addition of anisole (6.5 mL), the mixture was stirred at 20 to 25° C. for 1 hour and cooled to 3° C. over 2 hours. The crystals were filtered, washed with acetone (39 mL) cooled to 0° C., and then dried in vacuum at 55° C. to obtain the title compound as white crystals (21.58 g, 94.5%).

TABLE 2

| Production method | Compound IX (compound of interest)* | Compound X (diastereomer)* | Compounds XII and XIII (double bond positional isomers)* (total) | Compound XI (enantiomer)** |
|---|---|---|---|---|
| Patent Literature 6 | 98.03% | 0.04% | 1.54% | 1.47% |
| Example 35 | 99.84% | Not detected | 0.07% | 0.84% |
| Example 36 | 99.98% | Not detected | 0.01% | 0.00% |
| Example 37 | 99.90% | Not detected | 0.03% | 0.08% |
| Example 38 | 99.92% | Not detected | 0.06% | 0.09% |
| Example 39 | 99.96% | Not detected | 0.02% | 0.02% |

*Based on purity measurement method described in Example 35
**Analysis value obtained using chiral column Reference Example 1

Ethyl [(1R,5S,6S)-3-ethyl-6-(nitromethyl)bicyclo[3.2.0]hept-3-en-6-yl]acetate

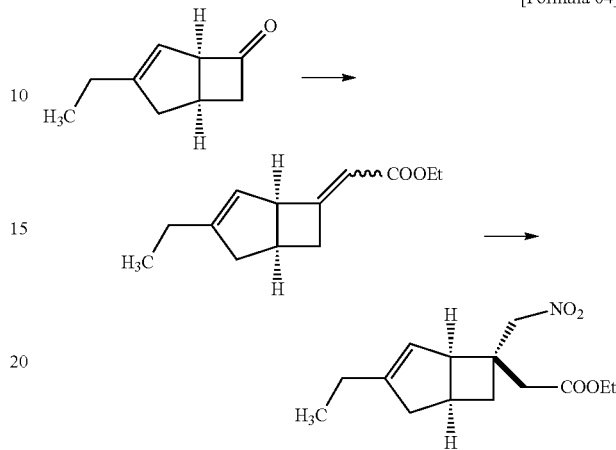

[Formula 64]

Sodium t-butoxide (7.41 g, 77.1 mmol) was dissolved in THF (50 mL). The solution was cooled to 10° C. or lower. Then, EPE (17.3 g, 77.1 mmol) and (1R,5S)-3-ethyl-bicyclo[3.2.0]hept-3-en-6-one (10.0 g, 73.4 mmol) were each added dropwise thereto. The mixture was stirred at room temperature for 3 hours, and toluene (85 mL) and water (40 mL) were then added thereto. The aqueous layer was removed, and the organic layer was then washed with water (20 mL) twice and concentrated to obtain ethyl [(1R,5S)-3-ethyl-bicyclo[3.2.0]hept-3-en-6-ylidene]acetate (14.4 g, 95%, E/Z=7/3) as an oil.

The oil (13.0 g) was dissolved in DMSO (60 mL). To the solution, DBU (8.96 g, 110 mmol) and nitromethane (8.96 g, 147 mmol) were added at room temperature. The mixture was stirred at 60° C. for 3 hours, and water (60 mL) and toluene (120 mL) were then added thereto. The aqueous layer was removed, and the organic layer was then washed with water (60 mL) twice and concentrated to obtain the title compound (6.4 g, 97%, diastereomeric ratio: 87:13).

$^1$H NMR (500 MHz, CDCl$_3$): δ=1.08 (t, 2.6H, J=7.4 Hz), 1.09 (t, 0.39H, J=7.4 Hz), 1.27 (t, 2.6H, J=7.4 Hz), 1.27 (t, 0.39H, J=7.4 Hz), 1.54 (dd, 0.87H, J=12.6, 7.4 Hz), 1.56 (s, 0.26H), 1.63 (dd, 0.13H, J=12.6, 7.4 Hz), 2.06 (d, 1H, J=16.6 Hz), 2.12-2.16 (m, 2H), 2.30 (ddd, 0.87H, J=11.5, 9.2, 2.9 Hz), 2.49-2.54 (m, 1H), 2.57 (s, 1.7H), 2.77 (d, 0.26H, J=4.6 Hz), 2.88 (quint, 0.87H, J=7.4 Hz), 3.17 (bs, 0.13H), 3.23 (bs, 0.87H), 4.11-4.18 (m, 2H), 4.57 (d, 0.13H, J=12.6 Hz), 4.65 (d, 0.13H, J=12.6 Hz), 4.78 (d, 0.87H, J=11.5 Hz), 4.85 (d, 0.87H, J=11.5 Hz), 5.25-5.26 (m, 0.87H), 5.36-5.37 (m, 0.13H).

Reference Example 2

[(1RS,5SR,6SR)-3-Ethyl-6-(nitromethyl)bicyclo[3.2.0]hept-3-en-6-yl]acetic acid (racemate)

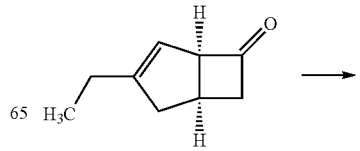

[Formula 65]

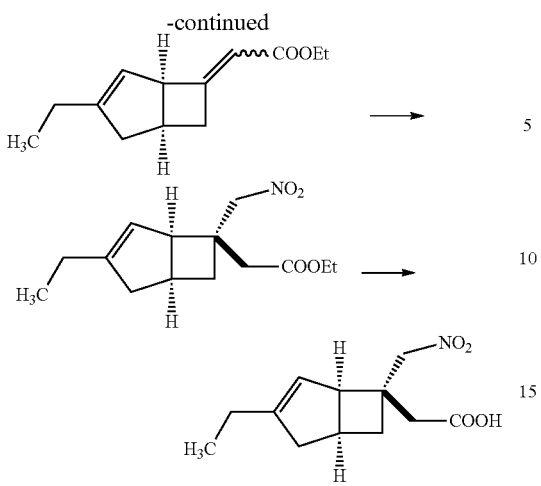

Sodium hydride (16.2 g, 407 mmol) was added to THF (500 mL), and the mixture was cooled to 10° C. or lower. EPE (90.5 g, 407 mmol) and (1RS,5SR)-3-ethyl-bicyclo[3.2.0]hept-3-en-6-one (50.0 g, 370 mmol) were each added dropwise thereto. After the completion of the dropwise addition, the mixture was stirred at room temperature for 19 hours, and water (150 mL) was then added thereto. The aqueous layer was removed, and the organic layer was then washed with saturated saline (100 mL) and concentrated. DMSO (200 mL) was further added to the residue, and the mixture was dehydrated and concentrated to obtain a crude product of ethyl [(1RS,5SR)-3-ethyl-bicyclo[3.2.0]hept-3-en-6-ylidene]acetate (308.9 g, E/Z=75/25) as a DMSO solution.

To the DMSO solution, DBU (111.8 g, 740 mmol) and nitromethane (89.6 g, 1480 mmol) were added at room temperature. The mixture was stirred under heating at 60° C. for 5 hours and then allowed to cool, and water (300 mL) and ethyl acetate (300 mL) were added thereto. The aqueous layer was removed, and the organic layer was then washed with water (300 mL) and concentrated to obtain ethyl [(1RS,5SR,6SR)-3-ethyl-6-(nitromethyl)bicyclo[3.2.0]hept-3-en-6-yl]acetate (104.3 g, 71% de) as an oil.

The oil was dissolved in EtOH (100 mL). To the solution, a 5 mol/L aqueous sodium hydroxide solution (250 mL) was added, and the mixture was stirred at 30° C. for 2 hours. To this reaction solution, toluene (150 mL) was added for separation into aqueous and organic layers. To the separated aqueous layer, 6 mol/L hydrochloric acid (220 mL) and ethyl acetate (200 mL) were added. After separation into aqueous and organic layers, the aqueous layer was further subjected to re-extraction with ethyl acetate (200 mL). The organic layers were mixed, dehydrated by the addition of magnesium sulfate, filtered, and then concentrated. The concentrated residue was crystallized at 5° C. to obtain a crude product of the title compound (89.2 g). A 40.0 g aliquot of the obtained crude product was suspended in a mixed solution of hexane:ethyl acetate=10:1 (200 mL) at room temperature, and the suspension was then stirred at 0° C. After 1 hour, the suspension was filtered and washed with a cold mixed solution of hexane:ethyl acetate=10:1 (40 mL). The obtained crystals were dried to obtain a single diastereomer of the title compound (22.4 g) as crystals.

$^1$H NMR (400 MHz, CDCl$_3$): δ=1.09 (t, 3H, J=7.6 Hz), 1.47-1.57 (m 2H), 2.06-2.17 (m, 3H), 2.27-2.33 (m, 1H), 2.49-2.55 (m, 1H), 2.66 (s, 2H), 2.88 (quint, 1H, J=7.6 Hz), 3.17 (bs, 1H), 4.78 (d, 1H, J=11.5 Hz), 4.86 (d, 1H, J=11.5 Hz), 5.27-5.28 (m, 1H).

The invention claimed is:

1. A mixture of compounds of formulas (I) and (I'):

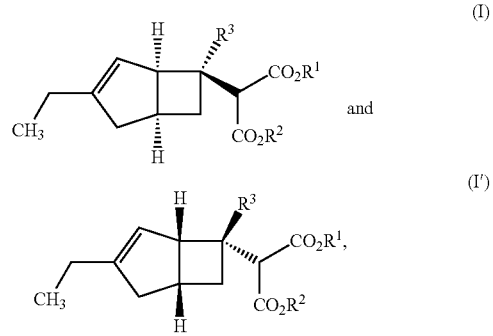

wherein $R^1$ and $R^2$ are each independently selected from a hydrogen atom and a C1-6 alkyl group, or $R^1$ and $R^2$ are bonded to each other to form an isopropylidene group; and $R^3$ is a cyano group or a nitromethyl group.

2. A compound of formula (I) or (I'):

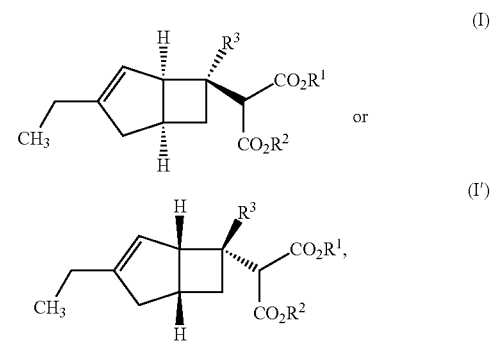

wherein $R^1$ and $R^2$ are each independently selected from a hydrogen atom and a C1-6 alkyl group, or $R^1$ and $R^2$ are bonded to each other to form an isopropylidene group; and $R^3$ is a cyano group or a nitromethyl group.

3. A method of producing a compound of formula (Ia), an enantiomer thereof, or both a compound of formula (Ia) and an enantiomer thereof, comprising mixing a compound of formula (II), an enantiomer thereof, or both a compound of formula (II) and an enantiomer thereof, with an alkali metal salt of hydrogen cyanide in a solvent to produce the compound of formula (Ia), an enantiomer thereof, or both a compound of formula (Ia) and an enantiomer thereof:

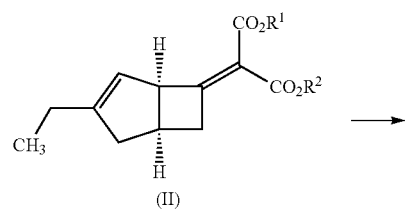

-continued

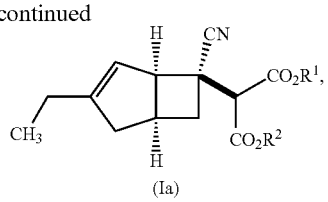

(Ia)

wherein $R^1$ and $R^2$ are each independently selected from a hydrogen atom and a C1-6 alkyl group, or $R^1$ and $R^2$ are bonded to each other to form an isopropylidene group.

4. A method of producing a compound of formula (Ib), an enantiomer thereof, or both a compound of formula (Ib) and an enantiomer thereof, comprising mixing a compound of formula (II), an enantiomer thereof, or both a compound of formula (II) and an enantiomer thereof, with nitromethane in the presence of a base in a solvent to produce the compound of formula (Ib), an enantiomer thereof, or both a compound of formula (Ib) and an enantiomer thereof:

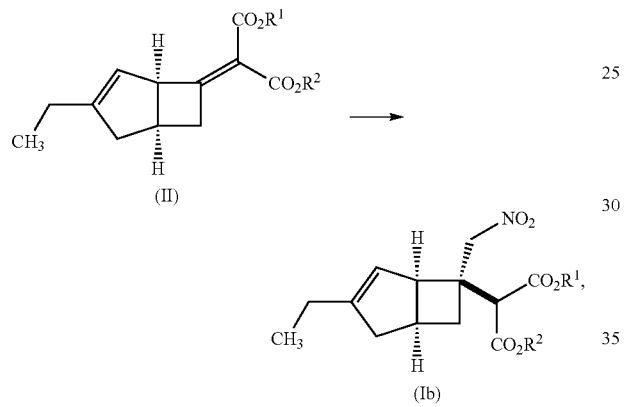

wherein $R^1$ and $R^2$ are each independently selected from a hydrogen atom and a C1-6 alkyl group, or $R^1$ and $R^2$ are bonded to each other to form an isopropylidene group.

5. A method of producing a compound of formula (Ia), an enantiomer thereof, or both a compound of formula (Ia) and an enantiomer thereof, comprising producing a compound of formula (II), an enantiomer thereof, or both a compound of formula (II) and an enantiomer thereof, from a compound of formula (III), an enantiomer thereof, or both a compound of formula (III) and an enantiomer thereof, and a compound of formula (IV) using a Lewis acid, and producing the compound of formula (Ia), an enantiomer thereof, or both a compound of formula (Ia) and an enantiomer thereof, from the compound of formula (II), an enantiomer thereof, or both a compound of formula (II) and an enantiomer thereof, by the method of claim 3:

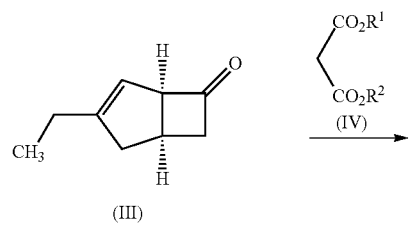

-continued

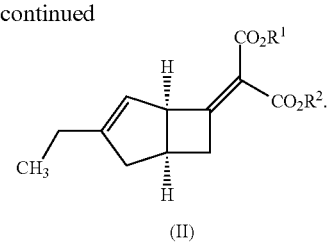

(II)

6. A method of producing a compound of formula (V), an enantiomer thereof, or both a compound of formula (V) and an enantiomer thereof, comprising treating a compound of formula (I), an enantiomer thereof, or both a compound of formula (I) and an enantiomer thereof, with a base in a solvent to produce the compound of formula (V), an enantiomer thereof, or both a compound of formula (V) and an enantiomer thereof:

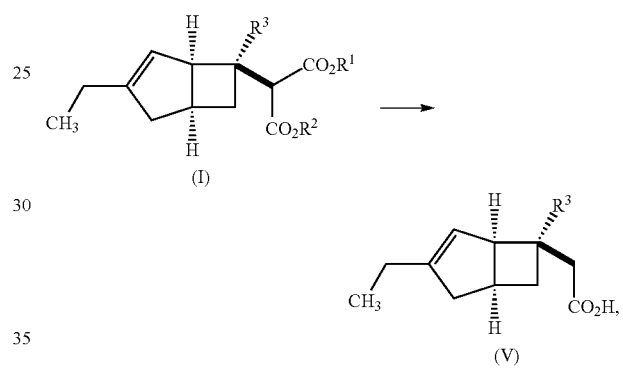

wherein $R^1$ and $R^2$ are each independently selected from a hydrogen atom and a C1-6 alkyl group; and
$R^3$ is a cyano group or a nitromethyl group.

7. A method of separating a compound of formula (V) and a compound of formula (V'), comprising allowing a mixture of the compound of formula (V) and the compound of formula (V') to form a salt with an optically active organic amine:

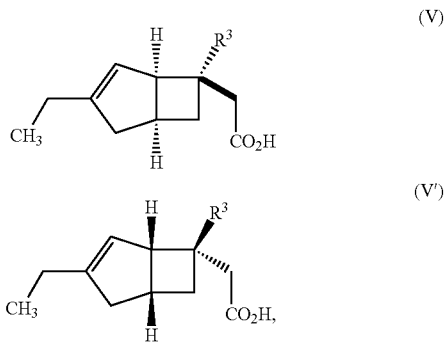

wherein $R^3$ is a cyano group or a nitromethyl group.

8. A method of producing a compound of formula (VI), comprising allowing a compound of formula (V) to form a salt with an organic amine in the presence of a solvent:

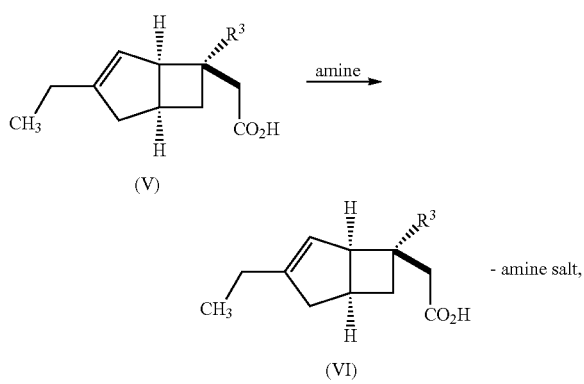

wherein R³ is a cyano group or a nitromethyl group.

9. The method of claim 8, wherein
R³ is a nitromethyl group,
the organic amine is an optically active organic amine, and
a racemic mixture of the compound of formula (V) and the compound of formula (V') is optically resolved.

10. A method of producing a compound of formula (VII) from a compound of formula (V) or (VI), comprising
reducing the compound of formula (V) in the presence of a metal catalyst in a solvent under a hydrogen atmosphere, or
subjecting a solution of the compound of formula (V) obtained through the salt dissociation of the compound of formula (VI) to a reduction reaction in the presence of a metal catalyst under a hydrogen atmosphere
to produce the compound of formula (VII):

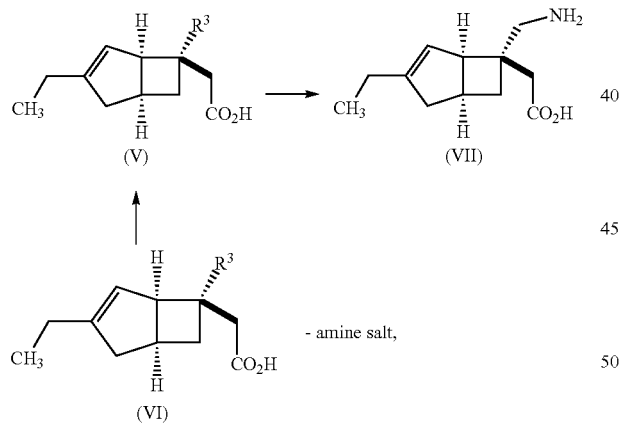

wherein R³ is a cyano group or a nitromethyl group.

11. The method of claim 10, comprising
converting the compound of formula (VI) to a compound of formula (V) through salt dissociation, and
subjecting the compound of formula (V) to a reduction reaction in the presence of a metal catalyst in a solvent under a hydrogen atmosphere to produce the compound represented by the formula (VII).

12. The method of claim 10, wherein the metal catalyst is a sponge nickel catalyst or a sponge cobalt catalyst.

13. The method of claim 10, wherein R³ is a cyano group.

14. The method of claim 10,
wherein the solvent is water, and
the reduction reaction is performed under basic conditions by the addition of a hydroxide of an alkali metal.

15. The method of claim 11, wherein
the metal catalyst is a sponge nickel catalyst or a sponge cobalt catalyst,
R³ is a cyano group,
the solvent is water, and
the reduction reaction is performed under basic conditions by the addition of a hydroxide of an alkali metal.

16. A method of producing a compound of formula (Ib), an enantiomer thereof, or both a compound of formula (Ia) and an enantiomer thereof:

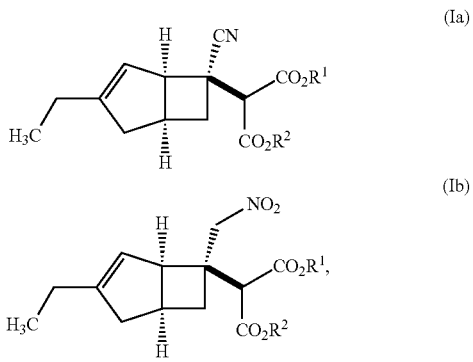

comprising
producing a compound of formula (II), an enantiomer thereof, or both a compound of formula (II) and an enantiomer thereof, from a compound of formula (III), an enantiomer thereof, or both a compound of formula (III) and an enantiomer thereof, and a compound of formula (IV) using a Lewis acid, and
producing the compound of formula (Ib), an enantiomer thereof, or both a compound of formula (Ia) and an enantiomer thereof, from the compound of formula (II), an enantiomer thereof, or both a compound of formula (II) and an enantiomer thereof, by the method of claim 3 or 4:

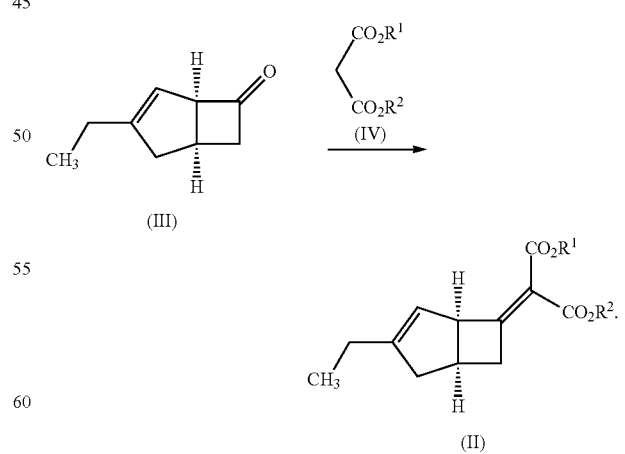

* * * * *